(12) United States Patent
Kostamo et al.

(10) Patent No.: US 9,423,360 B1
(45) Date of Patent: Aug. 23, 2016

(54) OPTICAL COMPONENTS

(71) Applicants: Pasi Kostamo, Espoo (FI); Ari J. Tervonen, Vantaa (FI)

(72) Inventors: Pasi Kostamo, Espoo (FI); Ari J. Tervonen, Vantaa (FI)

(73) Assignee: Microsoft Technology Licensing, LLC, Redmond, WA (US)

( * ) Notice: Subject to any disclaimer, the term of this patent is extended or adjusted under 35 U.S.C. 154(b) by 0 days.

(21) Appl. No.: 14/617,735

(22) Filed: Feb. 9, 2015

(51) Int. Cl.
| | |
|---|---|
| *G01B 11/00* | (2006.01) |
| *G01N 21/958* | (2006.01) |
| *G01N 21/88* | (2006.01) |
| *G01N 21/95* | (2006.01) |

(52) U.S. Cl.
CPC .......... *G01N 21/958* (2013.01); *G01N 21/8851* (2013.01); *G01N 2021/9511* (2013.01)

(58) Field of Classification Search
CPC ............... G03F 9/00; G02B 5/00; G02F 1/00; H01L 23/00; G01B 11/00; G06T 5/00; G01N 23/00
USPC .......................................... 356/399–401, 138
See application file for complete search history.

(56) References Cited

U.S. PATENT DOCUMENTS

| | | | |
|---|---|---|---|
| 3,227,888 A | 1/1966 | Turnbull et al. | |
| 3,542,453 A | 11/1970 | Kantor | |
| 3,836,258 A | 9/1974 | Courten et al. | |
| 3,906,528 A | 9/1975 | Johnson | |
| 3,971,085 A | 7/1976 | Mount | |
| 4,200,395 A | 4/1980 | Stewart et al. | |
| 4,294,507 A | 10/1981 | Johnson | |
| 4,402,610 A * | 9/1983 | Lacombat | G03F 9/7049 356/400 |
| 4,664,524 A * | 5/1987 | Hattori | G03F 9/7049 250/237 G |
| 4,711,512 A | 12/1987 | Upatnieks | |
| 4,758,087 A | 7/1988 | Hicks, Jr. | |

(Continued)

FOREIGN PATENT DOCUMENTS

| | | |
|---|---|---|
| CN | 1440513 | 9/2003 |
| CN | 101029968 | 9/2007 |

(Continued)

OTHER PUBLICATIONS

"Advisory Action", U.S. Appl. No. 13/428,879, Sep. 19, 2014, 3 pages.

(Continued)

*Primary Examiner* — Tarifur Chowdhury
*Assistant Examiner* — Isiaka Akanbi
(74) *Attorney, Agent, or Firm* — Micah Goldsmith; Judy Yee; Micky Minhas

(57) ABSTRACT

The following relates to assessing the quality of an optical component. The optical component comprises an arrangement of a first and a second optically transmissive component grating having a component relative orientation angle, and the quality is assessed in terms of a deviation of the component relative orientation angle from a desired relative orientation angle. A master component comprises a substantially matching arrangement of a first and a second optically transmissive master grating having the desired relative orientation angle. The components are supported with the first and second component gratings in the vicinity of the first and second master gratings, and first and second fringe patterns formed by the first gratings and second gratings respectively are used to output a quality assessment, which is based on the fringe spacing of the second fringe pattern when the fringe spacing of the first fringe pattern is substantially maximal.

20 Claims, 5 Drawing Sheets

(56) References Cited

U.S. PATENT DOCUMENTS

| | | | |
|---|---|---|---|
| 4,799,752 A | 1/1989 | Carome | |
| 4,822,145 A | 4/1989 | Staelin | |
| 4,860,361 A | 8/1989 | Sato et al. | |
| 4,900,129 A | 2/1990 | Vanderwerf | |
| 4,957,351 A | 9/1990 | Shioji | |
| 5,004,673 A | 4/1991 | Vlannes | |
| 5,019,808 A | 5/1991 | Prince et al. | |
| 5,019,898 A | 5/1991 | Chao et al. | |
| 5,106,181 A | 4/1992 | Rockwell, III | |
| 5,114,236 A * | 5/1992 | Matsugu | G03F 9/7076 250/548 |
| 5,146,355 A | 9/1992 | Prince et al. | |
| 5,162,656 A * | 11/1992 | Matsugu | G03F 9/7049 250/548 |
| 5,309,169 A | 5/1994 | Lippert | |
| 5,313,535 A | 5/1994 | Williams | |
| 5,359,444 A | 10/1994 | Piosenka et al. | |
| 5,413,884 A | 5/1995 | Koch et al. | |
| 5,453,877 A | 9/1995 | Gerbe et al. | |
| 5,455,458 A | 10/1995 | Quon et al. | |
| 5,459,611 A | 10/1995 | Bohn et al. | |
| 5,483,307 A | 1/1996 | Anderson | |
| 5,543,588 A | 8/1996 | Bisset et al. | |
| 5,549,212 A | 8/1996 | Kanoh et al. | |
| 5,574,473 A | 11/1996 | Sekiguchi | |
| 5,579,830 A | 12/1996 | Giammaruti | |
| 5,583,609 A | 12/1996 | Mizutani et al. | |
| 5,606,455 A | 2/1997 | Eichenlaub | |
| 5,614,941 A | 3/1997 | Hines | |
| 5,630,902 A | 5/1997 | Galarneau et al. | |
| 5,648,643 A | 7/1997 | Knowles et al. | |
| 5,651,414 A | 7/1997 | Suzuki et al. | |
| 5,673,146 A | 9/1997 | Kelly | |
| 5,708,449 A | 1/1998 | Heacock et al. | |
| 5,712,995 A | 1/1998 | Cohn | |
| 5,714,967 A | 2/1998 | Okamura et al. | |
| 5,737,171 A | 4/1998 | Buller et al. | |
| 5,751,476 A | 5/1998 | Matsui et al. | |
| 5,771,042 A | 6/1998 | Santos-Gomez | |
| 5,771,320 A | 6/1998 | Stone | |
| 5,772,903 A | 6/1998 | Hirsch | |
| 5,856,842 A | 1/1999 | Tedesco | |
| 5,861,931 A | 1/1999 | Gillian et al. | |
| 5,880,725 A | 3/1999 | Southgate | |
| 5,886,822 A | 3/1999 | Spitzer | |
| 5,940,149 A | 8/1999 | Vanderwerf | |
| 5,959,664 A | 9/1999 | Woodgate | |
| 5,982,553 A | 11/1999 | Bloom et al. | |
| 5,991,087 A | 11/1999 | Rallison | |
| 6,101,008 A | 8/2000 | Popovich | |
| 6,144,439 A | 11/2000 | Carollo | |
| 6,160,667 A | 12/2000 | Smoot | |
| 6,169,829 B1 | 1/2001 | Laming et al. | |
| 6,181,852 B1 | 1/2001 | Adams et al. | |
| 6,226,178 B1 | 5/2001 | Broder et al. | |
| 6,239,502 B1 | 5/2001 | Grewe et al. | |
| 6,271,808 B1 | 8/2001 | Corbin | |
| 6,307,142 B1 | 10/2001 | Allen et al. | |
| 6,323,949 B1 | 11/2001 | Lading et al. | |
| 6,323,970 B1 | 11/2001 | Popovich | |
| 6,377,401 B1 | 4/2002 | Bartlett | |
| 6,411,512 B1 | 6/2002 | Mankaruse et al. | |
| 6,417,892 B1 | 7/2002 | Sharp et al. | |
| 6,446,442 B1 | 9/2002 | Batchelor et al. | |
| 6,466,198 B1 | 10/2002 | Feinstein | |
| 6,470,289 B1 | 10/2002 | Peters et al. | |
| 6,481,851 B1 | 11/2002 | McNelley et al. | |
| 6,483,580 B1 | 11/2002 | Xu et al. | |
| 6,496,218 B2 | 12/2002 | Takigawa et al. | |
| 6,529,331 B2 | 3/2003 | Massof et al. | |
| 6,542,307 B2 | 4/2003 | Gleckman et al. | |
| 6,545,650 B1 | 4/2003 | Yamada et al. | |
| 6,553,165 B1 | 4/2003 | Temkin et al. | |
| 6,554,428 B2 | 4/2003 | Fergason et al. | |
| 6,577,411 B1 | 6/2003 | David | |
| 6,580,529 B1 | 6/2003 | Amitai et al. | |
| 6,606,152 B2 | 8/2003 | Littau | |
| 6,621,702 B2 | 9/2003 | Elias et al. | |
| 6,631,755 B1 | 10/2003 | Kung et al. | |
| 6,635,999 B2 | 10/2003 | Belliveau | |
| 6,639,201 B2 | 10/2003 | Almogy et al. | |
| 6,661,436 B2 | 12/2003 | Barksdale et al. | |
| 6,735,499 B2 | 5/2004 | Ohki et al. | |
| 6,753,828 B2 | 6/2004 | Tuceryan et al. | |
| 6,775,460 B2 | 8/2004 | Steiner et al. | |
| 6,792,328 B2 | 9/2004 | Laughery et al. | |
| 6,804,115 B2 | 10/2004 | Lai | |
| 6,809,925 B2 | 10/2004 | Belady et al. | |
| 6,819,426 B2 * | 11/2004 | Sezginer | G03F 7/70633 356/400 |
| 6,825,987 B2 | 11/2004 | Repetto et al. | |
| 6,829,095 B2 | 12/2004 | Amitai | |
| 6,867,753 B2 | 3/2005 | Chinthammit et al. | |
| 6,888,613 B2 | 5/2005 | Robins et al. | |
| 6,889,755 B2 | 5/2005 | Zuo et al. | |
| 6,906,901 B1 | 6/2005 | Liu | |
| 6,916,584 B2 | 7/2005 | Sreenivasan et al. | |
| 6,919,867 B2 | 7/2005 | Sauer | |
| 6,947,020 B2 | 9/2005 | Kiser et al. | |
| 6,964,731 B1 | 11/2005 | Krisko et al. | |
| 6,971,443 B2 | 12/2005 | Kung et al. | |
| 6,992,738 B2 | 1/2006 | Ishihara et al. | |
| 6,997,241 B2 | 2/2006 | Chou et al. | |
| 7,006,215 B2 | 2/2006 | Hoff et al. | |
| 7,015,876 B1 | 3/2006 | Miller | |
| 7,031,894 B2 | 4/2006 | Niu et al. | |
| 7,048,385 B2 | 5/2006 | Beeson et al. | |
| 7,061,624 B2 * | 6/2006 | Ishizuka | G01D 5/345 356/494 |
| 7,069,975 B1 | 7/2006 | Haws et al. | |
| 7,099,005 B1 | 8/2006 | Fabrikant et al. | |
| 7,113,605 B2 | 9/2006 | Rui et al. | |
| 7,116,555 B2 | 10/2006 | Kamath et al. | |
| 7,151,635 B2 | 12/2006 | Bidnyk et al. | |
| 7,181,699 B2 | 2/2007 | Morrow et al. | |
| 7,184,615 B2 | 2/2007 | Levola | |
| 7,189,362 B2 | 3/2007 | Nordin et al. | |
| 7,191,820 B2 | 3/2007 | Chou et al. | |
| 7,193,584 B2 | 3/2007 | Lee | |
| 7,196,758 B2 | 3/2007 | Crawford et al. | |
| 7,212,709 B2 | 5/2007 | Hosoi | |
| 7,212,723 B2 | 5/2007 | McLeod et al. | |
| 7,250,930 B2 | 7/2007 | Hoffman et al. | |
| 7,261,453 B2 | 8/2007 | Morejon et al. | |
| 7,261,827 B2 | 8/2007 | Ootsu et al. | |
| 7,271,795 B2 | 9/2007 | Bradski | |
| 7,277,282 B2 | 10/2007 | Tate | |
| 7,301,587 B2 | 11/2007 | Uehara et al. | |
| 7,333,690 B1 | 2/2008 | Peale et al. | |
| 7,337,018 B2 | 2/2008 | Espinoza-Ibarra et al. | |
| 7,359,420 B2 | 4/2008 | Shchegrov et al. | |
| 7,365,734 B2 | 4/2008 | Fateh et al. | |
| 7,369,101 B2 | 5/2008 | Sauer et al. | |
| 7,372,565 B1 | 5/2008 | Holden et al. | |
| 7,376,852 B2 | 5/2008 | Edwards | |
| 7,396,133 B2 | 7/2008 | Burnett et al. | |
| 7,412,306 B2 | 8/2008 | Katoh et al. | |
| 7,416,017 B2 | 8/2008 | Haws et al. | |
| 7,417,617 B2 | 8/2008 | Eichenlaub | |
| 7,418,170 B2 | 8/2008 | Mukawa et al. | |
| 7,428,001 B2 | 9/2008 | Schowengerdt et al. | |
| 7,430,349 B2 | 9/2008 | Jones | |
| 7,430,355 B2 | 9/2008 | Heikenfeld et al. | |
| 7,437,678 B2 | 10/2008 | Awada et al. | |
| 7,455,102 B2 | 11/2008 | Cheng | |
| 7,505,269 B1 | 3/2009 | Cosley et al. | |
| 7,513,627 B2 | 4/2009 | Larson et al. | |
| 7,515,143 B2 | 4/2009 | Keam et al. | |
| 7,532,227 B2 | 5/2009 | Nakajima et al. | |
| 7,542,665 B2 | 6/2009 | Lei | |
| 7,551,814 B1 | 6/2009 | Smits | |
| 7,576,916 B2 | 8/2009 | Amitai | |
| 7,583,327 B2 | 9/2009 | Takatani | |
| 7,607,111 B2 | 10/2009 | Vaananen et al. | |

(56) References Cited

U.S. PATENT DOCUMENTS

| | | |
|---|---|---|
| 7,612,882 B2 | 11/2009 | Wu et al. |
| 7,619,895 B1 | 11/2009 | Wertz et al. |
| 7,631,687 B2 | 12/2009 | Yang |
| 7,646,606 B2 | 1/2010 | Rytka et al. |
| 7,649,594 B2 | 1/2010 | Kim et al. |
| 7,656,912 B2 | 2/2010 | Brueck et al. |
| 7,660,500 B2 | 2/2010 | Konttinen et al. |
| 7,679,641 B2 | 3/2010 | Lipton et al. |
| 7,693,292 B1 | 4/2010 | Gross et al. |
| 7,701,716 B2 | 4/2010 | Blanco, Jr. et al. |
| 7,706,785 B2 | 4/2010 | Lei et al. |
| 7,716,003 B1 | 5/2010 | Wack et al. |
| 7,719,769 B2 | 5/2010 | Sugihara et al. |
| 7,728,933 B2 | 6/2010 | Kim et al. |
| 7,768,534 B2 | 8/2010 | Pentenrieder et al. |
| 7,777,944 B2 | 8/2010 | Ho et al. |
| 7,788,474 B2 | 8/2010 | Switzer et al. |
| 7,817,104 B2 | 10/2010 | Ryu et al. |
| 7,826,508 B2 | 11/2010 | Reid et al. |
| 7,832,885 B2 | 11/2010 | Hsiao et al. |
| 7,843,691 B2 | 11/2010 | Reichert et al. |
| 7,871,811 B2 | 1/2011 | Fang et al. |
| 7,890,882 B1 | 2/2011 | Nelson |
| 7,894,613 B1 | 2/2011 | Ong et al. |
| 7,903,409 B2 | 3/2011 | Patel et al. |
| 7,904,832 B2 | 3/2011 | Ubillos |
| 7,909,958 B2 | 3/2011 | Washburn et al. |
| 7,941,231 B1 | 5/2011 | Dunn |
| 7,986,462 B2 | 7/2011 | Kobayashi et al. |
| 8,004,621 B2 | 8/2011 | Woodgate et al. |
| 8,014,644 B2 | 9/2011 | Morimoto et al. |
| 8,033,709 B2 | 10/2011 | Kao et al. |
| 8,046,616 B2 | 10/2011 | Edwards |
| 8,061,411 B2 | 11/2011 | Xu et al. |
| 8,085,948 B2 | 12/2011 | Thomas et al. |
| 8,092,064 B2 | 1/2012 | Erchak et al. |
| 8,125,579 B2 | 2/2012 | Khan et al. |
| 8,128,800 B2 | 3/2012 | Seo et al. |
| 8,139,504 B2 | 3/2012 | Mankins et al. |
| 8,150,893 B2 | 4/2012 | Bohannon et al. |
| 8,160,411 B2 | 4/2012 | Levola et al. |
| 8,162,524 B2 | 4/2012 | Van Ostrand et al. |
| 8,165,988 B2 | 4/2012 | Shau et al. |
| 8,176,436 B2 | 5/2012 | Arend et al. |
| 8,195,220 B2 | 6/2012 | Kim et al. |
| 8,233,204 B1 | 7/2012 | Robbins et al. |
| 8,233,273 B2 | 7/2012 | Chen et al. |
| 8,244,667 B1 | 8/2012 | Weinberger et al. |
| 8,246,170 B2 | 8/2012 | Yamamoto et al. |
| 8,274,614 B2 | 9/2012 | Yokote et al. |
| 8,300,614 B2 | 10/2012 | Ankaiah et al. |
| 8,332,402 B2 | 12/2012 | Forstall et al. |
| 8,358,400 B2 | 1/2013 | Escuti |
| 8,384,999 B1 | 2/2013 | Crosby et al. |
| 8,392,035 B2 | 3/2013 | Patel et al. |
| 8,395,898 B1 | 3/2013 | Chamseddine et al. |
| 8,418,083 B1 | 4/2013 | Lundy et al. |
| 8,434,019 B2 | 4/2013 | Nelson |
| 8,446,340 B2 | 5/2013 | Aharoni |
| 8,472,119 B1 | 6/2013 | Kelly |
| 8,482,920 B2 | 7/2013 | Tissot et al. |
| 8,571,539 B1 | 10/2013 | Ranganathan et al. |
| 8,576,143 B1 | 11/2013 | Kelly |
| 8,589,341 B2 | 11/2013 | Golde et al. |
| 8,594,702 B2 | 11/2013 | Naaman et al. |
| 8,605,700 B2 | 12/2013 | Gurin |
| 8,611,014 B2 | 12/2013 | Valera et al. |
| 8,627,228 B2 | 1/2014 | Yosef et al. |
| 8,629,815 B2 | 1/2014 | Brin et al. |
| 8,638,498 B2 | 1/2014 | Bohn et al. |
| 8,645,871 B2 | 2/2014 | Fong et al. |
| 8,666,212 B1 | 3/2014 | Amirparviz |
| 8,693,500 B2 | 4/2014 | Ludwig et al. |
| 8,698,845 B2 | 4/2014 | Lemay |
| 8,700,931 B2 | 4/2014 | Gudlavenkatasiva et al. |
| 8,712,598 B2 | 4/2014 | Dighde et al. |
| 8,754,831 B2 | 6/2014 | Kollin et al. |
| 8,810,600 B2 | 8/2014 | Bohn et al. |
| 8,817,350 B1 | 8/2014 | Robbins et al. |
| 8,823,531 B1 | 9/2014 | McCleary et al. |
| 8,909,384 B1 | 12/2014 | Beitelmal et al. |
| 8,917,453 B2 | 12/2014 | Bohn |
| 8,934,235 B2 | 1/2015 | Rubenstein et al. |
| 8,941,683 B2 | 1/2015 | Son et al. |
| 8,989,535 B2 | 3/2015 | Robbins |
| 9,304,235 B2 | 4/2016 | Sainiema et al. |
| 9,372,347 B1 | 6/2016 | Levola et al. |
| 2001/0043208 A1 | 11/2001 | Furness, III et al. |
| 2002/035455 A1 | 3/2002 | Niu et al. |
| 2002/0038196 A1 | 3/2002 | Johnson et al. |
| 2002/0041735 A1 | 4/2002 | Cai et al. |
| 2002/0044152 A1 | 4/2002 | Abbott et al. |
| 2002/0044162 A1 | 4/2002 | Sawatari |
| 2002/0063820 A1 | 5/2002 | Broer et al. |
| 2002/0097558 A1 | 7/2002 | Stone et al. |
| 2002/0138772 A1 | 9/2002 | Crawford et al. |
| 2002/0171939 A1 | 11/2002 | Song |
| 2002/0180659 A1 | 12/2002 | Takahashi |
| 2003/0006364 A1 | 1/2003 | Katzir et al. |
| 2003/0023889 A1 | 1/2003 | Hofstee et al. |
| 2003/0137706 A1 | 7/2003 | Rmanujam et al. |
| 2003/0179453 A1 | 9/2003 | Mori et al. |
| 2003/0214728 A1 | 11/2003 | Olczak |
| 2004/0011503 A1 | 1/2004 | Kung et al. |
| 2004/0042724 A1 | 3/2004 | Gombert et al. |
| 2004/0085649 A1 | 5/2004 | Repetto et al. |
| 2004/0108971 A1 | 6/2004 | Waldern et al. |
| 2004/0109234 A1 | 6/2004 | Levola |
| 2004/0135209 A1 | 7/2004 | Hsieh et al. |
| 2004/0151466 A1 | 8/2004 | Crossman-Bosworth et al. |
| 2004/0176928 A1 | 9/2004 | Johnson |
| 2004/0267990 A1 | 12/2004 | Lin |
| 2005/0100272 A1 | 5/2005 | Gilman |
| 2005/0174737 A1 | 8/2005 | Meir |
| 2005/0207120 A1 | 9/2005 | Tseng et al. |
| 2005/0243107 A1 | 11/2005 | Haim et al. |
| 2005/0248705 A1 | 11/2005 | Smith et al. |
| 2005/0285878 A1 | 12/2005 | Singh et al. |
| 2006/0018025 A1 | 1/2006 | Sharon et al. |
| 2006/0032616 A1 | 2/2006 | Yang |
| 2006/0038881 A1 | 2/2006 | Starkweather et al. |
| 2006/0054787 A1 | 3/2006 | Olsen et al. |
| 2006/0072206 A1 | 4/2006 | Tsuyuki et al. |
| 2006/0118280 A1 | 6/2006 | Liu |
| 2006/0129951 A1 | 6/2006 | Vaananen et al. |
| 2006/0132806 A1 | 6/2006 | Shchegrov et al. |
| 2006/0132914 A1 | 6/2006 | Weiss et al. |
| 2006/0139447 A1 | 6/2006 | Unkrich |
| 2006/0152646 A1 | 7/2006 | Schrader |
| 2006/0164382 A1 | 7/2006 | Kulas et al. |
| 2006/0183331 A1 | 8/2006 | Hofmann |
| 2006/0196643 A1 | 9/2006 | Hata et al. |
| 2006/0221448 A1 | 10/2006 | Nivon et al. |
| 2006/0228073 A1 | 10/2006 | Mukawa et al. |
| 2006/0249765 A1 | 11/2006 | Hsieh |
| 2007/0002412 A1 | 1/2007 | Aihara |
| 2007/0008456 A1 | 1/2007 | Lesage et al. |
| 2007/0023703 A1 | 2/2007 | Sunaoshi et al. |
| 2007/0027591 A1 | 2/2007 | Goldenberg et al. |
| 2007/0041684 A1 | 2/2007 | Popovich et al. |
| 2007/0097019 A1 | 5/2007 | Wynne-Powell et al. |
| 2007/0147673 A1 | 6/2007 | Crandall |
| 2007/0153395 A1 | 7/2007 | Repetto et al. |
| 2007/0177260 A1 | 8/2007 | Kuppenheimer et al. |
| 2007/0236959 A1 | 10/2007 | Tolbert |
| 2007/0284093 A1 | 12/2007 | Bhatti et al. |
| 2008/0008076 A1* | 1/2008 | Raguin .............. G11B 7/0065 369/103 |
| 2008/0014534 A1 | 1/2008 | Barwicz et al. |
| 2008/0025350 A1 | 1/2008 | Arbore et al. |
| 2008/0043100 A1 | 2/2008 | Sobel et al. |
| 2008/0043425 A1 | 2/2008 | Hebert et al. |
| 2008/0088603 A1 | 4/2008 | Eliasson et al. |
| 2008/0088624 A1 | 4/2008 | Long et al. |

(56) References Cited

U.S. PATENT DOCUMENTS

| | | |
|---|---|---|
| 2008/0106677 A1 | 5/2008 | Kuan et al. |
| 2008/0117341 A1 | 5/2008 | McGrew |
| 2008/0141681 A1 | 6/2008 | Arnold |
| 2008/0150913 A1 | 6/2008 | Bell et al. |
| 2008/0174735 A1 | 7/2008 | Quach et al. |
| 2008/0232680 A1 | 9/2008 | Berestov et al. |
| 2008/0248852 A1 | 10/2008 | Rasmussen |
| 2008/0285140 A1 | 11/2008 | Amitai |
| 2008/0297535 A1 | 12/2008 | Reinig |
| 2008/0303918 A1 | 12/2008 | Keithley |
| 2008/0311386 A1 | 12/2008 | Wendt |
| 2009/0002939 A1 | 1/2009 | Baugh et al. |
| 2009/0015742 A1 | 1/2009 | Liao et al. |
| 2009/0021908 A1 | 1/2009 | Patel et al. |
| 2009/0051283 A1 | 2/2009 | Cok et al. |
| 2009/0059376 A1 | 3/2009 | Hayakawa |
| 2009/0084525 A1 | 4/2009 | Satou et al. |
| 2009/0092261 A1 | 4/2009 | Bard |
| 2009/0097127 A1 | 4/2009 | Amitai |
| 2009/0128449 A1 | 5/2009 | Brown et al. |
| 2009/0128901 A1 | 5/2009 | Tilleman et al. |
| 2009/0180250 A1 | 7/2009 | Holling et al. |
| 2009/0189974 A1 | 7/2009 | Deering |
| 2009/0190003 A1 | 7/2009 | Park et al. |
| 2009/0195756 A1 | 8/2009 | Li et al. |
| 2009/0222147 A1 | 9/2009 | Nakashima et al. |
| 2009/0224416 A1 | 9/2009 | Laakkonen et al. |
| 2009/0244413 A1 | 10/2009 | Ishikawa et al. |
| 2009/0246707 A1 | 10/2009 | Li et al. |
| 2009/0256837 A1 | 10/2009 | Deb et al. |
| 2009/0262419 A1 | 10/2009 | Robinson et al. |
| 2010/0002989 A1 | 1/2010 | Tokushima |
| 2010/0021108 A1 | 1/2010 | Kang et al. |
| 2010/0053151 A1 | 3/2010 | Marti et al. |
| 2010/0060551 A1 | 3/2010 | Sugiyama et al. |
| 2010/0061078 A1 | 3/2010 | Kim |
| 2010/0074291 A1 | 3/2010 | Nakamura |
| 2010/0084674 A1 | 4/2010 | Paetzold et al. |
| 2010/0096617 A1 | 4/2010 | Shanks |
| 2010/0103078 A1 | 4/2010 | Mukawa et al. |
| 2010/0134534 A1 | 6/2010 | Sesselberg et al. |
| 2010/0141905 A1 | 6/2010 | Burke |
| 2010/0149073 A1 | 6/2010 | Chaum et al. |
| 2010/0188353 A1 | 7/2010 | Yoon et al. |
| 2010/0200736 A1 | 8/2010 | Laycock et al. |
| 2010/0201953 A1 | 8/2010 | Freeman et al. |
| 2010/0213467 A1 | 8/2010 | Lee et al. |
| 2010/0220439 A1 | 9/2010 | Qin |
| 2010/0229853 A1 | 9/2010 | Vandal et al. |
| 2010/0238270 A1 | 9/2010 | Bjelkhagen et al. |
| 2010/0245387 A1 | 9/2010 | Bachelder et al. |
| 2010/0259889 A1 | 10/2010 | Chen et al. |
| 2010/0271467 A1 | 10/2010 | Akeley |
| 2010/0277421 A1 | 11/2010 | Charlier et al. |
| 2010/0277439 A1 | 11/2010 | Charlier et al. |
| 2010/0277779 A1 | 11/2010 | Futterer et al. |
| 2010/0284085 A1 | 11/2010 | Laakkonen |
| 2010/0300654 A1 | 12/2010 | Edwards |
| 2010/0309687 A1 | 12/2010 | Sampsell et al. |
| 2010/0315781 A1 | 12/2010 | Agostini |
| 2010/0317132 A1 | 12/2010 | Rogers et al. |
| 2010/0321609 A1 | 12/2010 | Qi et al. |
| 2010/0328351 A1 | 12/2010 | Tan |
| 2011/0012814 A1 | 1/2011 | Tanaka |
| 2011/0021251 A1 | 1/2011 | Lindén |
| 2011/0025605 A1 | 2/2011 | Kwitek |
| 2011/0026128 A1 | 2/2011 | Baker et al. |
| 2011/0032482 A1 | 2/2011 | Agurok |
| 2011/0050547 A1 | 3/2011 | Mukawa |
| 2011/0050655 A1 | 3/2011 | Mukawa |
| 2011/0063795 A1 | 3/2011 | Yeh et al. |
| 2011/0075442 A1 | 3/2011 | Chiang |
| 2011/0084893 A1 | 4/2011 | Lee et al. |
| 2011/0090343 A1 | 4/2011 | Alt et al. |
| 2011/0091156 A1 | 4/2011 | Laughlin |
| 2011/0114823 A1 | 5/2011 | Katzir et al. |
| 2011/0127024 A1 | 6/2011 | Patel et al. |
| 2011/0134017 A1 | 6/2011 | Burke |
| 2011/0134645 A1 | 6/2011 | Hitchcock et al. |
| 2011/0141388 A1 | 6/2011 | Park et al. |
| 2011/0148931 A1 | 6/2011 | Kim |
| 2011/0163986 A1 | 7/2011 | Lee et al. |
| 2011/0194029 A1 | 8/2011 | Herrmann et al. |
| 2011/0205251 A1 | 8/2011 | Auld |
| 2011/0210946 A1 | 9/2011 | Goertz et al. |
| 2011/0214082 A1 | 9/2011 | Osterhout et al. |
| 2011/0215349 A1 | 9/2011 | An et al. |
| 2011/0221658 A1 | 9/2011 | Haddick et al. |
| 2011/0221659 A1 | 9/2011 | King et al. |
| 2011/0222236 A1 | 9/2011 | Luo et al. |
| 2011/0227820 A1 | 9/2011 | Haddick et al. |
| 2011/0227913 A1 | 9/2011 | Hyndman |
| 2011/0235179 A1 | 9/2011 | Simmonds |
| 2011/0242145 A1 | 10/2011 | Nishimura et al. |
| 2011/0242392 A1 | 10/2011 | Chiang |
| 2011/0242757 A1 | 10/2011 | Tracy et al. |
| 2011/0248904 A1 | 10/2011 | Miyawaki et al. |
| 2011/0248958 A1 | 10/2011 | Gruhlke et al. |
| 2011/0267799 A1 | 11/2011 | Epstein et al. |
| 2011/0283223 A1 | 11/2011 | Vaittinen et al. |
| 2011/0295913 A1 | 12/2011 | Enbutsu |
| 2011/0299044 A1 | 12/2011 | Yeh et al. |
| 2011/0304640 A1 | 12/2011 | Noge |
| 2011/0309378 A1 | 12/2011 | Lau et al. |
| 2011/0310232 A1 | 12/2011 | Wilson et al. |
| 2011/0310312 A1 | 12/2011 | Yokote et al. |
| 2012/0013651 A1 | 1/2012 | Trayner et al. |
| 2012/0019434 A1 | 1/2012 | Kuhlman et al. |
| 2012/0026161 A1 | 2/2012 | Chen et al. |
| 2012/0030616 A1 | 2/2012 | Howes et al. |
| 2012/0033306 A1 | 2/2012 | Valera et al. |
| 2012/0038629 A1 | 2/2012 | Brown et al. |
| 2012/0041721 A1 | 2/2012 | Chen |
| 2012/0050144 A1 | 3/2012 | Morlock |
| 2012/0052934 A1 | 3/2012 | Maharbiz et al. |
| 2012/0062998 A1 | 3/2012 | Schultz et al. |
| 2012/0069413 A1 | 3/2012 | Schultz |
| 2012/0084710 A1 | 4/2012 | Sirpal et al. |
| 2012/0106170 A1 | 5/2012 | Matthews et al. |
| 2012/0111544 A1 | 5/2012 | Senatori |
| 2012/0113092 A1 | 5/2012 | Bar-Zeev et al. |
| 2012/0120493 A1 | 5/2012 | Simmonds et al. |
| 2012/0134623 A1 | 5/2012 | Boudreau et al. |
| 2012/0157114 A1 | 6/2012 | Alameh et al. |
| 2012/0162764 A1 | 6/2012 | Shimizu |
| 2012/0176322 A1 | 7/2012 | Karmi et al. |
| 2012/0176474 A1 | 7/2012 | Border |
| 2012/0182687 A1 | 7/2012 | Dighde et al. |
| 2012/0188205 A1 | 7/2012 | Jansson et al. |
| 2012/0195553 A1 | 8/2012 | Hasegawa et al. |
| 2012/0200495 A1 | 8/2012 | Johansson |
| 2012/0206589 A1 | 8/2012 | Crandall |
| 2012/0206880 A1 | 8/2012 | Andres et al. |
| 2012/0218301 A1 | 8/2012 | Miller |
| 2012/0227006 A1 | 9/2012 | Amm |
| 2012/0235885 A1 | 9/2012 | Miller et al. |
| 2012/0242561 A1 | 9/2012 | Sugihara |
| 2012/0256856 A1 | 10/2012 | Suzuki et al. |
| 2012/0256963 A1 | 10/2012 | Suzuki et al. |
| 2012/0262657 A1 | 10/2012 | Nakanishi et al. |
| 2012/0287381 A1 | 11/2012 | Li et al. |
| 2012/0292535 A1 | 11/2012 | Choi et al. |
| 2012/0304092 A1 | 11/2012 | Jarrett et al. |
| 2013/0000871 A1 | 1/2013 | Olson et al. |
| 2013/0033485 A1 | 2/2013 | Kollin et al. |
| 2013/0081779 A1 | 4/2013 | Liao et al. |
| 2013/0093741 A1 | 4/2013 | Akimoto et al. |
| 2013/0106592 A1 | 5/2013 | Morgan et al. |
| 2013/0106674 A1 | 5/2013 | Wheeler et al. |
| 2013/0148864 A1 | 6/2013 | Dolson et al. |
| 2013/0162673 A1 | 6/2013 | Bohn |
| 2013/0163089 A1 | 6/2013 | Bohn |
| 2013/0170031 A1 | 7/2013 | Bohn |
| 2013/0170802 A1 | 7/2013 | Pitwon |

(56) References Cited

U.S. PATENT DOCUMENTS

| | | |
|---|---|---|
| 2013/0186596 A1 | 7/2013 | Rubenstein |
| 2013/0186598 A1 | 7/2013 | Rubenstein |
| 2013/0187943 A1 | 7/2013 | Bohn et al. |
| 2013/0207964 A1 | 8/2013 | Fleck |
| 2013/0208003 A1 | 8/2013 | Bohn |
| 2013/0208362 A1 | 8/2013 | Bohn |
| 2013/0208482 A1 | 8/2013 | Fleck et al. |
| 2013/0215081 A1 | 8/2013 | Levin et al. |
| 2013/0226931 A1 | 8/2013 | Hazel et al. |
| 2013/0242056 A1 | 9/2013 | Fleck |
| 2013/0242555 A1 | 9/2013 | Mukawa |
| 2013/0250431 A1 | 9/2013 | Robbins et al. |
| 2013/0252628 A1 | 9/2013 | Kuehnel |
| 2013/0254412 A1 | 9/2013 | Menezes et al. |
| 2013/0257848 A1 | 10/2013 | Westerinen et al. |
| 2013/0258701 A1 | 10/2013 | Westerinen et al. |
| 2013/0267309 A1 | 10/2013 | Robbins |
| 2013/0294030 A1 | 11/2013 | Wang et al. |
| 2013/0305184 A1 | 11/2013 | Kim et al. |
| 2013/0307875 A1 | 11/2013 | Anderson |
| 2013/0314789 A1 | 11/2013 | Saarikko et al. |
| 2013/0314793 A1 | 11/2013 | Robbins |
| 2013/0322810 A1 | 12/2013 | Robbins |
| 2013/0332159 A1 | 12/2013 | Federighi et al. |
| 2013/0335671 A1 | 12/2013 | Fleck |
| 2013/0339446 A1 | 12/2013 | Balassanian et al. |
| 2013/0342674 A1 | 12/2013 | Dixon |
| 2013/0346725 A1 | 12/2013 | Lomet et al. |
| 2014/0010265 A1 | 1/2014 | Peng |
| 2014/0022265 A1 | 1/2014 | Canan et al. |
| 2014/0041827 A1 | 2/2014 | Giaimo |
| 2014/0059139 A1 | 2/2014 | Filev et al. |
| 2014/0063367 A1 | 3/2014 | Yang et al. |
| 2014/0078130 A1 | 3/2014 | Uchino et al. |
| 2014/0089833 A1 | 3/2014 | Hwang et al. |
| 2014/0094973 A1 | 4/2014 | Giaimo et al. |
| 2014/0098671 A1 | 4/2014 | Raleigh et al. |
| 2014/0104665 A1 | 4/2014 | Popovich et al. |
| 2014/0104685 A1 | 4/2014 | Bohn |
| 2014/0111865 A1 | 4/2014 | Kobayashi |
| 2014/0116982 A1 | 5/2014 | Schellenberg et al. |
| 2014/0140653 A1 | 5/2014 | Brown et al. |
| 2014/0140654 A1 | 5/2014 | Brown et al. |
| 2014/0143247 A1 | 5/2014 | Rathnavelu et al. |
| 2014/0143351 A1 | 5/2014 | Deng |
| 2014/0176528 A1 | 6/2014 | Robbins |
| 2014/0184699 A1 | 7/2014 | Ito et al. |
| 2014/0204455 A1 | 7/2014 | Popovich |
| 2014/0240842 A1 | 8/2014 | Nguyen et al. |
| 2014/0300966 A1 | 10/2014 | Travers et al. |
| 2014/0314374 A1 | 10/2014 | Fattal et al. |
| 2015/0086163 A1 | 3/2015 | Valera et al. |
| 2015/0168731 A1 | 6/2015 | Robbins |
| 2016/0033697 A1 | 2/2016 | Sainiemi et al. |
| 2016/0033784 A1 | 2/2016 | Levola et al. |
| 2016/0035539 A1 | 2/2016 | Sainiemi et al. |

FOREIGN PATENT DOCUMENTS

| | | |
|---|---|---|
| CN | 101105512 | 1/2008 |
| CN | 102004315 | 4/2011 |
| EP | 0977022 | 2/2000 |
| EP | 1494109 | 1/2005 |
| EP | 1847924 | 10/2007 |
| EP | 2065750 | 6/2009 |
| EP | 2083310 | 7/2009 |
| EP | 2112547 | 10/2009 |
| EP | 2144177 | 1/2010 |
| EP | 2216678 | 1/2010 |
| EP | 2241926 | 10/2010 |
| EP | 2662761 | 11/2013 |
| EP | 2752691 | 7/2014 |
| EP | 2887121 | 6/2015 |
| FR | 2942811 | 9/2010 |
| GB | 2500631 | 10/2013 |
| JP | 557109618 | 7/1982 |
| JP | H0422358 | 1/1992 |
| JP | 7311303 | 11/1995 |
| JP | 2000347037 | 12/2000 |
| JP | 2001078234 | 3/2001 |
| JP | 2008017135 | 1/2008 |
| KR | 20070001771 | 1/2007 |
| KR | 20090076539 | 7/2009 |
| KR | 20090084316 | 8/2009 |
| KR | 20110070087 | 6/2011 |
| KR | 20120023458 | 3/2012 |
| TW | 201407202 | 2/2014 |
| WO | WO-9418595 | 8/1994 |
| WO | WO 9952002 | 10/1999 |
| WO | WO-0133282 | 5/2001 |
| WO | WO-0195027 | 12/2001 |
| WO | WO-03090611 | 11/2003 |
| WO | WO-2006054056 | 5/2006 |
| WO | WO 2006064334 | 6/2006 |
| WO | WO 2007052265 | 5/2007 |
| WO | WO-2007057500 | 5/2007 |
| WO | WO-2008021504 | 2/2008 |
| WO | WO 2008081070 | 7/2008 |
| WO | WO 2009029826 | 3/2009 |
| WO | WO-2009077601 | 6/2009 |
| WO | WO 2009127849 | 10/2009 |
| WO | WO 2010092409 | 8/2010 |
| WO | WO-2010125337 | 11/2010 |
| WO | WO-2011003381 | 1/2011 |
| WO | WO 2011051660 | 5/2011 |
| WO | WO-2011051660 | 5/2011 |
| WO | WO-2011090455 | 7/2011 |
| WO | WO-2011110728 | 9/2011 |
| WO | WO-2011131978 | 10/2011 |
| WO | WO-2012172295 | 12/2012 |
| WO | WO-2012177811 | 12/2012 |
| WO | WO 2013033274 | 3/2013 |
| WO | WO-2013058769 | 4/2013 |
| WO | WO 2013164665 | 11/2013 |
| WO | WO-2014051920 | 4/2014 |
| WO | WO-2014085502 | 6/2014 |
| WO | WO-2014088343 | 6/2014 |
| WO | WO 2014111163 | 7/2014 |
| WO | WO-2014130383 | 8/2014 |

OTHER PUBLICATIONS

"Augmented Reality and Physical Games", U.S. Appl. No. 13/440,165, filed Apr. 5, 2012, 49 pages.

"BragGrate Mirror", Retrieved from <http://web.archive.org/web/20090814104232/http://www.optigrate.com/BragGrate_Mirror.html> on Jul. 8, 2014, Aug. 14, 2009, 2 pages.

"Corrected Final Office Action", U.S. Appl. No. 13/432,311, Dec. 24, 2014, 25 pages.

"Corrected Notice of Allowance", U.S. Appl. No. 13/355,836, Sep. 11, 2014, 2 pages.

"Corrected Notice of Allowance", U.S. Appl. No. 13/355,836, Dec. 15, 2014, 2 pages.

"DigiLens", SBG Labs—retrieved from <http://www.digilens.com/products.html> on Jun. 19, 2012, 1 page.

"Final Office Action", U.S. Appl. No. 13/336,873, Jan. 5, 2015, 21 pages.

"Final Office Action", U.S. Appl. No. 13/336,895, May 27, 2014, 11 pages.

"Final Office Action", U.S. Appl. No. 13/355,836, Mar. 10, 2014, 18 pages.

"Final Office Action", U.S. Appl. No. 13/355,914, Feb. 23, 2015, 21 pages.

"Final Office Action", U.S. Appl. No. 13/355,914, Jun. 19, 2014, 11 pages.

"Final Office Action", U.S. Appl. No. 13/397,495, May 29, 2014, 10 pages.

"Final Office Action", U.S. Appl. No. 13/397,516, Jan. 29, 2015, 13 pages.

"Final Office Action", U.S. Appl. No. 13/397,539, Jun. 29, 2015, 11 pages.

(56) References Cited

OTHER PUBLICATIONS

"Final Office Action", U.S. Appl. No. 13/428,879, Jul. 14, 2014, 12 pages.
"Final Office Action", U.S. Appl. No. 13/432,311, Dec. 15, 2014, 24 pages.
"Final Office Action", U.S. Appl. No. 13/432,372, Jan. 29, 2015, 33 pages.
"Final Office Action", U.S. Appl. No. 13/440,165, Jun. 6, 2014, 12 pages.
"Final Office Action", U.S. Appl. No. 13/440,165, Jul. 21, 2015, 11 pages.
"Final Office Action", U.S. Appl. No. 13/477,646, Feb. 23, 2015, 36 pages.
"Final Office Action", U.S. Appl. No. 13/477,646, May 5, 2014, 26 pages.
"Final Office Action", U.S. Appl. No. 13/525,649, Oct. 9, 2014, 8 pages.
"Final Office Action", U.S. Appl. No. 13/774,875, Jun. 4, 2015, 10 pages.
"Final Office Action", U.S. Appl. No. 14/134,993, Jul. 16, 2015, 19 pages.
"Final Office Action ", U.S. Appl. No. 14/134,993, Aug. 20, 2014, 15 pages.
"Foreign Notice of Allowance", CN Application No. 201320034345.X, Aug. 14, 2013, 2 Pages.
"Foreign Office Action", CN Application No. 201210563730.3, Jan. 7, 2015, 16 pages.
"Foreign Office Action", CN Application No. 201210567932.5, Aug. 14, 2014, 12 pages.
"Foreign Office Action", EP Application No. 13769961.7, Mar. 11, 2015, 8 pages.
"Foreign Office Action", EP Application No. 13769961.7, Jun. 30, 2015, 6 pages.
"HDTV Helmet Mounted Display", Available at <http://defense-update.com/products/h/HDTV-HMD.htm>, Jan. 26, 2005, 1 page.
"International Search Report and Written Opinion", Application No. PCT/US2012/069331, Mar. 29, 2013, 10 pages.
"International Search Report and Written Opinion", Application No. PCT/US2014/016658, Apr. 23, 2014, 10 pages.
"International Search Report and Written Opinion", Application No. PCT/US2013/053676, Oct. 16, 2013, 10 pages.
"International Search Report and Written Opinion", Application No. PCT/US2013/030632, Jun. 26, 2013, 10 pages.
"International Search Report and Written Opinion", Application No. PCT/US2013/028477, Jun. 21, 2013, 11 pages.
"International Search Report and Written Opinion", Application No. PCT/US2013/031111, Jun. 26, 2013, 11 pages.
"International Search Report and Written Opinion", Application No. PCT/US2013/076832, Mar. 17, 2014, 12 pages.
"International Search Report and Written Opinion", Application No. PCT/US2013/061225, Jun. 4, 2014, 12 pages.
"International Search Report and Written Opinion", Application No. PCT/US2012/071563, Apr. 25, 2013, 13 pages.
"International Search Report and Written Opinion", Application No. PCT/US2013/021784, Apr. 30, 2013, 9 pages.
"International Search Report and Written Opinion", Application No. PCT/US2012/069330, Mar. 28, 2013, 9 pages.
"International Search Report and Written Opinion", Application No. PCT/US2013/021783, May 15, 2013, 9 pages.
"International Search Report and Written Opinion", Application No. PCT/US2013/026200, Jun. 3, 2013, 9 pages.
"Light Guide Techniques using LED Lamps", Application Brief I-003, retrieved from <http://www.ciri.org.nz/downloads/Lightpipe%20design.pdf> on Jan. 12, 2012, Oct. 14, 2008, 22 pages.
"New Technology from MIT may Enable Cheap, Color, Holographic Video Displays", Retrieved from <http://www.gizmag.com/holograph-3d-color-video-display-inexpensive-mit/28029/> on Feb. 25, 2015, Jun. 24, 2013, 8 pages.
"Non-Final Office Action", U.S. Appl. No. 13/397,495, Nov. 13, 2013, 8 pages.
"Non-Final Office Action", U.S. Appl. No. 13/440,165, Feb. 6, 2014, 12 pages.
"Non-Final Office Action", U.S. Appl. No. 13/336,873, Apr. 9, 2015, 18 pages.
"Non-Final Office Action", U.S. Appl. No. 13/336,873, Jul. 25, 2014, 16 pages.
"Non-Final Office Action", U.S. Appl. No. 13/336,895, Oct. 24, 2013, 9 pages.
"Non-Final Office Action", U.S. Appl. No. 13/343,675, Jul. 16, 2013, 9 pages.
"Non-Final Office Action", U.S. Appl. No. 13/355,836, Nov. 4, 2013, 15 pages.
"Non-Final Office Action", U.S. Appl. No. 13/355,914, Feb. 14, 2014, 10 pages.
"Non-Final Office Action", U.S. Appl. No. 13/355,914, Oct. 28, 2014, 18 pages.
"Non-Final Office Action", U.S. Appl. No. 13/397,495, Apr. 3, 2015, 11 pages.
"Non-Final Office Action", U.S. Appl. No. 13/397,516, Jun. 12, 2014, 11 pages.
"Non-Final Office Action", U.S. Appl. No. 13/397,516, Nov. 25, 2013, 10 pages.
"Non-Final Office Action", U.S. Appl. No. 13/397,539, Mar. 16, 2015, 9 pages.
"Non-Final Office Action", U.S. Appl. No. 13/397,617, May 5, 2015, 6 pages.
"Non-Final Office Action", U.S. Appl. No. 13/397,617, Oct. 9, 2014, 6 pages.
"Non-Final Office Action", U.S. Appl. No. 13/428,879, Feb. 24, 2015, 10 pages.
"Non-Final Office Action", U.S. Appl. No. 13/428,879, Mar. 17, 2014, 10 pages.
"Non-Final Office Action", U.S. Appl. No. 13/428,879, Jun. 26, 2015, 13 pages.
"Non-Final Office Action", U.S. Appl. No. 13/432,311, Jun. 2, 2015, 25 pages.
"Non-Final Office Action", U.S. Appl. No. 13/432,311, Jul. 8, 2014, 33 pages.
"Non-Final Office Action", U.S. Appl. No. 13/432,372, May 9, 2014, 26 pages.
"Non-Final Office Action", U.S. Appl. No. 13/432,372, Oct. 24, 2014, 27 pages.
"Non-Final Office Action", U.S. Appl. No. 13/440,165, Feb. 13, 2015, 10 pages.
"Non-Final Office Action", U.S. Appl. No. 13/440,165, Oct. 16, 2014, 11 pages.
"Non-Final Office Action", U.S. Appl. No. 13/477,646, Jun. 18, 2015, 43 pages.
"Non-Final Office Action", U.S. Appl. No. 13/477,646, Oct. 6, 2014, 34 pages.
"Non Final Office Action", U.S. Appl. No. 13/477,646, Nov. 22, 2013, 20 pages.
"Non-Final Office Action", U.S. Appl. No. 13/525,649, Jan. 29, 2014, 7 pages.
"Non-Final Office Action", U.S. Appl. No. 13/525,649, Feb. 5, 2015, 7 pages.
"Non-Final Office Action", U.S. Appl. No. 13/525,649, Jun. 5, 2014, 7 pages.
"Non-Final Office Action", U.S. Appl. No. 13/570,073, Jan. 23, 2015, 7 pages.
"Non-Final Office Action", U.S. Appl. No. 13/631,308, Feb. 23, 2015, 9 pages.
"Non-Final Office Action", U.S. Appl. No. 13/722,917, May 21, 2015, 12 pages.
"Non-Final Office Action", U.S. Appl. No. 13/774,875, Nov. 24, 2014, 8 pages.
"Non-Final Office Action", U.S. Appl. No. 14/134,993, Jan. 22, 2015, 17 pages.
"Non-Final Office Action", U.S. Appl. No. 14/134,993, Apr. 17, 2014, 34 pages.
"Notice of Allowance", U.S. Appl. No. 13/336,895, Aug. 11, 2014, 6 pages.

(56) References Cited

OTHER PUBLICATIONS

"Notice of Allowance", U.S. Appl. No. 13/343,675, Sep. 16, 2013, 8 pages.
"Notice of Allowance", U.S. Appl. No. 13/355,836, Jun. 13, 2014, 11 pages.
"Notice of Allowance", U.S. Appl. No. 13/355,836, Oct. 8, 2014, 11 pages.
"Notice of Allowance", U.S. Appl. No. 13/356,545, Mar. 28, 2014, 6 pages.
"Notice of Allowance", U.S. Appl. No. 13/488,145, Nov. 19, 2014, 8 pages.
"Restriction Requirement", U.S. Appl. No. 13/355,836, Sep. 27, 2013, 6 pages.
"Restriction Requirement", U.S. Appl. No. 13/397,539, Dec. 1, 2014, 6 pages.
"Restriction Requirement", U.S. Appl. No. 13/488,145, Sep. 8, 2014, 14 pages.
"Restriction Requirement", U.S. Appl. No. 13/570,073, Nov. 18, 2014, 7 pages.
"Supplemental Notice of Allowance", U.S. Appl. No. 13/356,545, Jul. 22, 2014, 2 pages.
"Supplementary European Search Report", EP Application No. 13769961.7, Mar. 3, 2015, 3 pages.
"Two-Faced: Transparent Phone with Dual Touch Screens", Retrieved from <http://gajitz.com/two-faced-transparent-phone-with-dual-touch-screens/>, Jun. 7, 2012, 3 pages.
"Variable Groove Depth (VGD) Master Gratings", Retrieved From: <http://www.horiba.com/scientific/products/diffraction-gratings/catalog/variable-groove-depth-vgd/> May 28, 2014, 2 pages.
"Written Opinion", Application No. PCT/US2013/061225, Oct. 10, 2014, 6 Pages.
Allen,"ELIXIR—Solid-State Luminaire with Enhanced Light Extraction by Internal Reflection", Journal of Display Technology, vol. 3, No. 2, Available at <http://www.nanolab.uc.edu/Publications/PDFfiles/355.pdf>, Jun. 2007, pp. 155-159.
Aron,"'Sprinting' chips could push phones to the speed limit", New Scientist, Feb. 20, 2012, Issue #2852, Feb. 20, 2012, 2 pages.
Baluja, "Non-Intrusive Gaze Tracking Using Artificial Neural Networks", Technical Report CMU-CS-94-102, Available at <http://citeseerx.ist.psu.edu/viewdoc/download?doi=10.1.1.33.4027&rep=rep1&type=pdf>, Jan. 5, 1994, 14 pages.
Barger,"COTS Cooling", Publication of the National Electronics Manufacturing Center of Excellence, Retrieved from: <http://www.empf.org/empfasis/2009/Oct09/cots.html > on Jul. 9, 2012, Oct. 2009, 4 pages.
Baudisch,"Back-of-Device Interaction Allows Creating Very Small Touch Devices", In Proceedings of the 27th International Conference on Human Factors in Computing Systems, Retrieved from <http://citeseerx.ist.psu.edu/viewdoc/download?doi=10.1.1.160.3337&rep=rep1&type=pdf>, Apr. 2005, 10 pages.
Baxtor,"TwinTech GeForce GTS 250 XT OC 1GB Graphics Card", retrieved from <http://www.tweaktown.com/reviews/2733/twintech_geforce_gts_250_xt_oc_1gb_graphics_card/index3.html> on Dec. 30, 2011, Apr. 24, 2009, 4 pages.
Chang-Yen,"A Monolithic PDMS Waveguide System Fabricated Using Soft-Lithography Techniques", In Journal of Lightwave Technology, vol. 23, No. 6, Jun. 2005, 6 pages.
Charles,"Design of Optically Path Length Matched, Three-Dimensional Photonic Circuits Comprising Uniquely Routed Waveguides", In Proceedings of Applied Optics, vol. 51, Issue 27, Sep. 20, 2012, 11 pages.
Chen,"A Study of Fiber-to-Fiber Losses in Waveguid Grating Routers", In Journal of Lightwave Technology, vol. 15, No. 10, Oct. 1997, 5 pages.
Chen,"Strategies for 3D Video with Wide Fields-of-View", IEEE Proceeding Optoelectronics, vol. 148, Issue 2, Available at <http://ieeexplore.ieee.org/stamp/stamp.jsp?tp=&arnumber=926823>, Apr. 2001, pp. 85-90.
Cheng,"Waveguide Displays Based on Polymer-dispersed Liquid Crystals", SPIE Newsroom, Available at <http://spie.org/documents/Newsroom/Imported/003805/003805_10.pdf>, Aug. 12, 2011, 2 pages.
Chirgwin,"Researches propose to 'overclock' scheme for mobiles— Processing at a sprint to overcome tech limitations", The Register, Feb. 21, 2012, 2 pages.
Coldeway,"Researches Propose "Computational Sprinting" to Speed Up Chips by 1000%—But Only for a Second", TechCrunch, Feb. 28, 2012, Feb. 29, 2012, 2 pages.
Cottier,"Label-free Highly Sensitive Detection of (small) Molecules by Wavelength Interrogation of Integrated Optical Chips", n Proceedings of Sensors and Actuators B: Chemical, vol. 91, Issue 1-3, Jun. 1, 2003, pp. 241-251.
DeAgazio:"Selecting Display Backlighting for Portable, Handheld Devices", Hearst Electronics Products, retrieved from <http://www2.electronicproducts.com/Selecting_display_backlighting_for_portable_handheld_devices-article-farcglobal-feb2008-html.aspx> on Jan. 12, 2012, Jan. 2, 2008, 4 pages.
Dumon,"Compact Arrayed Waveguide Grating Devices in Silicon-on-Insulator", In Proceedings of the IEEE/LEOS Symposium Benelux Chapter, May 27, 2014, 4 pages.
Eadicicco,"First Transparent Tablet Lets You Touch From Both Sides", Retrieved from <http://blog.laptopmag.com/first-transparent-tablet>, Dec. 26, 2013, 4 pages.
Glendenning,"Polymer Micro-Optics via Micro Injection Moulding", Available at: https://web.archive.org/web/20120310003606/http://www.microsystems.uk.com/english/polymer_optics_injection_moulding.html, Jan. 10, 2011, 6 pages.
Grabarnik,"Concave Diffraction Gratings Fabricated With Planar Lithography," In Proceedings of SPIE, vol. 6992, May 3, 2008, 8 pages.
Greenemeier,"Could "Computational Sprinting" Speed Up Smart Phones without Burning Them Out?", Scientific American, Feb. 29, 2012, 2 pages.
Greiner,"Bandpass engineering of lithographically scribed channel-waveguide Bragg gratings", In Proceedings of Optics Letters, vol. 29, No. 8, Apr. 15, 2004, pp. 806-808.
Han,"Accurate diffraction efficiency control for multiplexed volume holographic gratings", Retrieved at: opticalengineering.spiedigitallibrary.org/data/Journals/.../2799_1, 2002, 4 pages.
Hua,"Engineering of Head-mounted Projective Displays", In Proceedings of Applied Optics, vol. 39, No. 22, Aug. 1, 2000, 11 pages.
Ismail,"Improved Arrayed-Waveguide-Grating Layout Avoiding Systematic Phase Errors", In Proceedings of Optics Express, vol. 19, No. 9, Apr. 25, 2011, pp. 8781-8794.
Jacques,"Polarized Light Imaging of Tissue", Available at <http://www.lumamed.com/documents/5_polarized%20light%20imaging.pdf>, 2004, 17 pages.
Jarvenpaa,"Compact near-to-eye display with integrated gaze tracker", Second International Conference on Computer Engineering and Applications, Mar. 19, 2010, 9 pages.
Jaworski,"A Novel Design of Heat Sink with PCM for Electronics Cooling", 10th International Conference on Thermal Energy Storage, Stockton, May 31-Jun. 2, 2006, retrieved from <https://intraweb.stockton.edu/eyos/energy_studies/content/docs/FINAL_PRESENTATIONS/4b-6%20.pdf> on Jan. 5, 2012, May 31, 2006, 8 pages.
Karp,"Planar Micro-optic Solar Concentration using Multiple Imaging Lenses into a Common Slab Waveguide", In Proceedings of SPIE vol. 7407, Available at <http://psilab.ucsd.edu/research/slab_concentration/files/SPIE_Slab_Published.pdf>, Jan. 2009, 11 pages.
Kress,"Exit Pupil for Wearable See-through displays", Downloaded From: http://proceeding.spiedigitallibrary.org/ on Jan. 31, 2015 Terms of Use: http://spiedl.org/terms, 2012, 8 pages.
Krishnan,"A Novel Hybrid Heat Sink Using Phase Change Materials for Transient Thermal Management of Electronics", IEEE transactions on components and packaging technologies, vol. 28, No. 2, retrieved from <http://ieeexplore.ieee.org/stamp/stamp.jsp?tp=&arnumber=1432936> on Jan. 5, 2012, Jun. 2005, pp. 281-289.
L,"All-Nanoparticle Concave Diffraction Grating Fabricated by Self-Assembly onto Magnetically-Recorded Templates", In Proceedings of Optical Express, vol. 21, Issue 1, Jan. 2013, 1 page.

(56) References Cited

OTHER PUBLICATIONS

Lanman,"Neareye Light Field Displays", In Journal of ACM Transactions on Graphics, vol. 32, No. 6, Nov. 2013, 10 pages.
Large,"Parallel Optics in Waveguide Displays: a Flat Panel Autostereoscopic", Display Technology, Journal of, Retrieved from <http://download.microsoft.com/download/D/2/E/D2E425F8-CF3C-4C71-A4A2-70F9D4081007/ParallelOpticsinWaveguideDisplaysMS090925.Final.pdf>, Jun. 21, 2010, pp. 1-7.
Lerner,"Penn Helps Rethink Smartphone Design With 'Computational Sprinting'", Penn News Release, Feb. 28, 2012, 2 pages.
Li,"Design Optimization of Reflective Polarizers for LCD Backlight Recycling", Journal of Display Technology, vol. 5, No. 8, Available at <http://ieeexplore.ieee.org/stamp/stamp.jsp?tp=&arnumber=5196840 >, Aug. 2009, pp. 335-340.
Li, "Switchable Electro-optic Diffractive Lens with High Efficiency for Ophthalmic Applications", PNAS Apr. 18, 2006 vol. 103 No. 16 6100-6104, Retrieved from: <http://www.pnas.org/content/103/16/6100.long> Feb. 22, 2012, Feb. 2, 2006, 4 pages.
Lindau,"Controlling the Groove Depth of Holographic Gratings", In Proceedings of Optical System Design, Analysis, and Production, vol. 0399, Oct. 26, 1983, 2 pages.
Man,"IT Equipment Noise Emission Standards: Overview of New Development in the Next Edition of ISO/ECMA Standards", In Proceedings of the 37th International Congress and Exposition on Noise Control Engineering, Available at <http://www.ecma-international.org/activities/Acoustics/Inter-noise%202008%20paper%20on%20ECMA-74%20updates.pdf 22 , Oct. 26, 2008, 8 pages.
Massenot,"Multiplexed holographic transmission gratings recorded in holographic polymer-dispersed liquid crystals: static and dynamic studies", Retrieved at: http://oatao.univ-toulouse.fr/2874/, 2005, 8 pages.
McMillon,"Your Future iPhone May Be Stuffed With Wax", Aug. 23, 2013, 3 pages.
Mei,"An all fiber interferometric gradient hydrophone with optical path length compensation", In Proceedings of Summaries of Papers Presented at the Conference on Lasers and Electro-Optics, May 28, 1999, 2 pages.
Melcher,"LCoS for High Performance Displays" In Proceedings of LEOS 2003, Available at <http://ieeexplore.ieee.org/stamp/stamp.jsp?tp=&arnumber=1253048>, Oct. 27, 2003, pp. 812-813.
Minier,"Diffraction Characteristics of Superimposed Holographic gratings in Planar Optical waveguides", IEEE Photonics Technology Letters, vol. 4, No. 10, Oct. 1992, 4 pages.
Moore,"Computational sprinting pushes smartphones till they're tired", Michigan News Release, Feb. 28, 2012, 2 pages.
Morga,"History of SAW Devices", In Proceedings of the IEEE International Frequency Control Symposium, May 27, 1998, 22 pages.
Nguyen,"Advanced Cooling System Using Miniature Heat Pipes in Mobile PC", IEEE Transactions on Components and Packaging Technology, vol. 23, No. 1, Available at <http://ieeexplore.ieee.org/stamp/stamp.jsp?tp=&arnumber=833046&userType=inst>, Mar. 2000, pp. 86-90.
Owano,"Study explores computing bursts for smartphones", PhysOrg.com, Feb. 21, 2012, 2 pages.
Papaefthymiou,"Computational Sprinting on a Hardware/Software Testbed", In the Proceedings of the 18th Eighteenth International Conference on Architectural Support for Programming Languages and Operating Systems (ASPLOS), Mar. 2013., 12 pages.
Patrizio,"Researchers Working on Ways to Put 16-Core Processors in Smartphones", Brighthand, Mar. 18, 2012, 2 pages.
Pu,"Exposure schedule for for multiplexing holograms in photopolymer films", Retrieved at: lo.epfl.ch/webdav/site/lo/shared/1996/OE_35_2824_Oct1996.pdf, Oct. 1996, 6 pages.
Raghavan,"Computatbnal Sprinting", In the Proceedings of the 18th Symposium on High Performance Computer Architecture (HPCA), Feb. 2012, 12 pages.
Raghavan,"Designing for Responsiveness With Computational Sprinting", IEEE Micro's "Top Picks of 2012" Issue, May 2013, 8 pages.
Scott,"RearType: Text Entry Using Keys on the Back of a Device", In Proceedings of 12th Conference on Human-Computer Interaction with Mobile Devices and Services, Retrieved from <https://research.microsoft.com/pubs/135609/reartype%20mobilehci.pdf>, Sep. 7, 2010, 9 pages.
Singh"Laser-Based Head-Tracked 3D Display Research", Journal of Display Technology, vol. 6, No. 10, Available at <http://ieeexplore.ieee.org/stamp/stamp.jsp?tp=arnumber=5462999>, Oct. 2010, pp. 531-543.
Smalley,"Anisotropic Leaky-Mode Modulator for Holographic Video Displays", In Proceedings of Nature, vol. 498, Jun. 20, 2013, 6 pages.
Stupar,"Optimization of Phase Change Material Heat Sinks for Low Duty Cycle High Peak Load Power Supplies", IEEE transactions on components, packaging and manufacturing technology, retrieved from <http://ieeexplore.ieee.org/stamp/stamp.jsp?tp=&arnumber=6081913> Jan. 5, 2012, Nov. 15, 2011, 14 pages.
Tari,"CFD Analyses of a Notebook Computer Thermal Management System and a Proposed Passive Cooling Alternative", IEEE Transactions on Components and Packaging Technologies, vol. 33, No. 2, retrieved from <http://ieeexplore.ieee.org/stamp/stamp.jsp?tp=&arnumber=5466211> on Dec. 30, 2011, Jun. 2010, pp. 443-452.
Teng,"Fabrication of nanoscale zero-mode waveguides using microlithography for single molecule sensing", In Proceedings of Nanotechnology, vol. 23, No. 45, Jul. 7, 2012, 7 pages.
Tien,"Microcontact Printing of SAMs", In Proceedings of Thin Films, vol. 24, May 28, 2014, 24 pages.
Travis,"Collimated Light from a Waveguide for a Display Backlight", Optics Express—Retrieved from <http://download.microsoft.com/download/D/2/E/D2E425F8-CF3C-4C71-A4A2-70F9D4081007/OpticsExpressbacklightpaper.pdf>, Oct. 15, 2009, pp. 19714-19719.
Travis,"The Design of Backlights for View-Sequential", Microsoft Corporation, Available at <http://download.microsoft.com/download/D/2/E/D2E425F8-CF3C-4C71-A4A2-70F9D4081007/Backlightforviewsequentialautostereo.docx>, Jul. 3, 2010, 4 pages.
Van"A Survey of Augmented Reality Technologies, Applications and Limitations", The International Journal of Virtual Reailty, 2010, 9(2), Available at <http://www.ijvr.org/issues/issue2-2010/paper1%20.pdf>, Jun. 2010, pp, 1-19.
Walker,"Thermalright Ultra-120 Extreme CPU Cooler", retrieved from <http://www.pro-clockers.com/cooling/66-thermalright-ultra-120-extreme-cpu-cooler.html> on Dec. 30, 2011, Jul. 2, 2009, 7 pages.
Westerinen,"Light Guide Display and Field of View", U.S. Appl. No. 13/428,879, filed Mar. 23, 2012, 46 pages.
Wigdor,"LucidTouch: A See-Through Mobile Device", In Proceedings of 20th Annual ACM symposium on User Interface Software and Technology, Retrieved from <http://dl.acm.org/citation.cfm?id=1294259>, Oct. 7, 2007, 10 pages.
Xie,"Fabrication of Varied-Line-Spacing Grating by Elastic Medium", In Proceedings SPIE 5636, Holography, Diffractive Optics, and Applications II, Nov. 2004, 4 pages.
Yan,"Multiplexing holograms in the photopolymer with equal diffraction efficiency", 2005, 9 pages.
Zharkova,"Study of the Dynamics of Transmission Gratings Growth on Holographic Polymer-Dispersed Liquid Crystals", International Conference on Methods of Aerophysical Research, ICMAR 2008, 2008, 4 pages.
"International Search Report and Written Opinion", Application No. PCT/US2015/041930, Oct. 20, 2015, 12 Pages.
"International Search Report and Written Opinion", Application No. PCT/US2015/041900, Oct. 21, 2015, 12 pages.
"International Search Report and Written Opinion", Application No. PCT/US2015/041909, Oct. 20, 2015, 13 pages.
"Non-Final Office Action", U.S. Appl. No. 13/774,875, Sep. 16, 2015, 8 pages.
"Notice of Allowance", U.S. Appl. No. 14/447,464, Nov. 9, 2015, 10 pages.

(56) References Cited

OTHER PUBLICATIONS

"Restriction Requirement", U.S. Appl. No. 14/617,697, Nov. 30, 2015, 6 pages.
Ando, "Development of Three Dimensional Microstrages Using Inclined Deep-Reactive Ion Etching", Journal of Microelectomechanical Systems, Jun. 1, 2007, 10 pages.
Gila,"First Results From a Multi-Ion Beam Lithography and Processing System at The University of Florida", AIP Conference Proceedings, Jun. 1, 2011, 6 pages.
"International Search Report and Written Opinion", Application No. PCT/US2015/042371, Oct. 2, 2015, 10 pages.
"International Search Report and Written Opinion", Application No. PCT/US2015/042187, Oct. 20, 2015, 10 pages.
"International Search Report and Written Opinion", Application No. PCT/US2015/042226, Oct. 27, 2015, 10 Pages.
"International Search Report and Written Opinion", Application No. PCT/US2015/042205, Oct. 30, 2015, 10 pages.
"International Search Report and Written Opinion", Application No. PCT/US2015/042218, Nov. 6, 2015, 10 pages.
"International Search Report and Written Opinion", Application No. PCT/US2015/042259, Oct. 12, 2015, 11 pages.
"International Search Report and Written Opinion", Application No. PCT/US2015/041046, Nov. 9, 2015, 15 pages.
"Non-Final Office Action", U.S. Appl. No. 14/447,419, Feb. 2, 2016, 8 pages.
"Non-Final Office Action", U.S. Appl. No. 14/617,574, Feb. 26, 2016, 22 pages.
"Non-Final Office Action", U.S. Appl. No. 14/617,710, Mar. 2, 2016, 16 pages.
"Notice of Allowance", U.S. Appl. No. 14/617,697, Feb. 29, 2016, 7 pages.
"Notice of Allowance", U.S. Appl. No. 14/617,723, Feb. 9, 2016, 10 pages.
"Supplemental Notice of Allowance", U.S. Appl. No. 14/447,464, Jan. 12, 2016, 2 pages.
Antonopoulos,"Efficient Updates for Web-Scale Indexes over the Cloud", IEEE 28th International Conference on Data Engineering Workshops, Apr. 2012, 8 pages.
Garcia,"COMET: Content Mediator Architecture for Content-Aware Networks", In IEEE Future Network & Mobile Summit, 2011, 8 pages.
Levandoski,"Ranking and New Database Architectures", In Proceedings of the 7th International Workshop on Ranking in Databases, Aug. 2013, 4 pages.
"Adobe Audition / Customizing Workspaces", Retrieved From: <http://help.adobe.com/en_US/audition/cs/using/WS9FA7B8D7-5991-4e05-B13C-4C85DAF1F051.html> Jul. 5, 2014, May 18, 2011, 6 Pages.
"Always Connected", Available at: http://www.samsung.com/global/microsite/galaxycamera/nx/, Jun. 24, 2013, 5 pages.
"Controlling Your Desktop's Power Management", Retrieved From: <http://www.vorkon.de/SU1210.001/drittanbieter/Dokumentation/openSUSE_11.2/manual/sec.gnomeuser.start.power_mgmt.html> Jul. 7, 2014, 6 Pages.
"Display Control", Retrieved From: <http://www.portrait.com/technology/display-control.html> Jul. 4, 2014, Jun. 24, 2013, 5 Pages.
"Manage Multiple Windows", Retrieved From: <http://windows.microsoft.com/en-hk/windows/manage-multiple-windows#1TC=windows-7> Jul. 8, 2014, 4 Pages.
"Merge Operator", Retrieved on: Jun. 3, 2014, Available at: https://github.com/facebook/rocksdb/wiki/Merge-Operator, 10 pages.
"Organize Your Desktop Workspace for More Comfort with WindowSpace.", Retrieved From: <http://www.ntwind.com/software/windowspace.html> Jul. 4, 2014, Sep. 19, 2008, 5 pages.
"Restriction Requirement", U.S. Appl. No. 14/447,419, Aug. 4, 2015, 6 pages.
"SizeUp the Missing Window Manager", Retrieved From: <https://www.irradiatedsoftware.com/sizeup/> Jul. 4, 2014, Jan. 17, 2013, 4 Pages.

"Using Flickr to Organize a Collection of Images", Available at: http://www.jiscdigitalmedia.ac.uk/guide/using-flickr-to-organise-a-collection-of-images, Apr. 2, 2013, 17 pages.
"Window Magnet", Retrieved From: <http://magnet.crowdcafe.com/> Jul. 4, 2014, Jun. 23, 2011, 2 Pages.
"Windows 7: Display Reminder When Click on Shutdown?", Retrieved From: <http://www.sevenforums.com/customization/118688-display-reminder-when-click-shutdown.html> Jul. 8, 2014, Oct. 18, 2010, 5 Pages.
"Working with Windows", Retrieved From: <http://windows.microsoft.com/en-us/windows/working-with-windows#1TC=windows-7> Jul. 4, 2014, 10 Pages.
Ashraf,"Winsplit Revolution: Tile, Resize, and Position Windows for Efficient Use of Your Screen," Retrieved From: <http://dottech.org/11240/winsplit-revolution-tile-resize-and-position-windows-for-efficient-use-of-your-screen/> Jul. 8, 2014, Dec. 18, 2011, 4 Pages.
Callaghan,"Types of writes", Available at: http://smalldatum.blogspot.in/2014/04/types-of-writes.html, Apr. 17, 2014, 3 pages.
Cohen, "Automatic Stratagies in the Siemens RTL Tiled Window Manager", In Proceedings: The 2nd IEEE Conference on Computer Workstations, Mar. 7, 1988, pp. 111-119.
Eckel, "Personalize Alerts with the Help of OS X Mavericks Notifications", Retrieved From: <http://www.techrepublic.com/article/customize-os-x-mavericks-notifications-to-personalize-alerts/> Jul. 8, 2014, Mar. 10, 2014, 7 Pages.
Elnaka,"Real-Time Traffic Classification for Unified Communication Networks", In Proceedings of International Conference on Selected Topics in Mobile and Wireless Networking, Aug. 19, 2013, 6 pages.
Hepburn,"Color: The Location used Social Photo App", Available at: http://www.digitalbuzzblog.com/color-the-location-based-social-photo-iphone-app/, Mar. 27, 2011, 12 pages.
Johnson,"Samsung Galaxy Tab Pro 10.1 Review", Retrieved From: <http://hothardware.com/Review/Samsung-Galaxy-Tab-Pro-101-Review/?page=3#!baG2DY > Jul. 9, 2014, Mar. 21, 2014, 10 Pages.
Kandogan,"Elastic Windows: Improved Spatial Layout and Rapid Multiple Window Operations", In Proceedings of the Workshop on Advanced Visual Interfaces, May 27, 1996, 10 Pages.
Levandoski, "Latch-Free, Log-Structured Storage for Multiple Access Methods", U.S. Appl. No. 13/924,567, filed Jun. 22, 2013, 51 pages.
Levandoski,"The Bw-Tree: A B-tree for New Hardware Platforms", In IEEE 29th International Conference on Data Engineering, Apr. 8, 2013, 12 pages.
Li,"QRON: QoS-Aware Routing in Overlay Networks", In Proceedings of IEEE Journal on Selected Areas in Communications, vol. 22, No. 1, Jan. 2004, 12 pages.
Mack,"Moto X: The First Two Weeks" , Retrieved From: <http://www.gizmag.com/two-weeks-motorola-google-moto-x-review/28722/> Jul. 8, 2014, Aug. 16, 2013, 8 pages.
O'Reilly,"How to Use the Microsoft Surface Touch Screen and Keyboard", Retrieved From: <http://www.cnet.com/how-to/how-to-use-the-microsoft-surface-touch-screen-and-keyboard/> Jul. 5, 2014, Nov. 6, 2012, 5 Pages.
Paut,"Three Windows Multitasking Features That Help Maximize Your Screen Space", Retrieved From: <http://www.pcworld.com/article/2094124/three-windows-multitasking-features-that-help-maximize-your-screen-space.html> Jul. 4, 2014, Feb. 4, 2014, 4 Pages.
Prohaska,"Fast Updates with TokuDB", Available at: http://www.tokutek.com/2013/02/fast-updates-with-tokudb/, Feb. 12, 2013, 2 pages.
Thurrott,"Nokia Lumia "Black", Glance 2.0", Retrieved From:<http://winsupersite.com/windows-phone/nokia-lumia-black-glance-20> Jul. 8, 2014, Jan. 11, 2014, 3 Pages.
Vranjes,"Application Window Divider Control for Window Layout Management", U.S. Appl. No. 13/863,369, filed Apr. 15, 2013, 21 pages.
Wiebe,"Using screen space efficiently with Gridmove". Available at: http://lowerthought.wordpress.com/2010/05/15/using-screen-space-efficiently-with-gridmove/, May 15, 2010, 2 pages.
Corrected Notice of Allowance, U.S. Appl. No. 14/617,723, Apr. 20, 2016, 7 pages.

(56) References Cited

OTHER PUBLICATIONS

Final Office Action, U.S. Appl. No. 13/774,875, Apr. 22, 2016, 10 pages.
Final Office Action, U.S. Appl. No. 14/447,419, May 17, 2016, 10 pages.
International Search Report and Written Opinion, Application No. PCT/US2016/015496, Apr. 11, 2016, 11 pages.
International Search Report and Written Opinion, Application No. PCT/US2016/015873, May 23, 2016, 11 pages.
International Search Report and Written Opinion, Application No. PCT/US2016/016028, May 25, 2016, 11 pages.
International Search Report and Written Opinion, Application No. PCT/US2016/016241, Apr. 20, 2016, 12 pages.
International Search Report and Written Opinion, Application No. PCT/US2016/015869, May 12, 2016, 12 pages.
International Search Report and Written Opinion, Application No. PCT/US2016/016029, May 12, 2016, 12 pages.
International Search Report and Written Opinion, Application No. PCT/US2016/016027, May 17, 2016, 13 pages.
International Search Report and Written Opinion, Application No. PCT/US2016/019006, May 12, 2016, 14 pages.
International Search Report and Written Opinion, Application No. PCT/US2016/016242, May 27, 2016, 14 pages.
International Search Report and Written Opinion, Application No. PCT/US2016/015497, May 19, 2016, 17 pages.
Non-Final Office Action, U.S. Appl. No. 14/335,927, Jun. 3, 2016, 8 pages.
Non-Final Office Action, U.S. Appl. No. 14/617,606, May 23, 2016, 12 pages.
Notice of Allowance, U.S. Appl. No. 14/617,723, May 24, 2016, 7 pages.
Notice of Allowance, U.S. Appl. No. 14/617,746, Apr. 11, 2016, 7 pages.
Restriction Requirement, U.S. Appl. No. 14/617,683, May 9, 2016, 6 pages.
Kim,"Determination of small angular displacement by moire fringes of matched radial-parallel gratings", Applied Optics, vol. 36, No. 13, May 1997, 8 pages.
Levola,"Diffractive optics for virtual reality displays", Journal of the Society for Information Display—SID, Jan. 1, 2006, 9 pages.
Theocaris,"Radial Gratings as Moire Gauges", Journal of Physics E. Scientific Instruments, Jun. 1, 1968, 6 pages.
International Search Report and Written Opirtion, Application No. PCT/US2016/015871, Jun. 13, 2016, 13 pages.

\* cited by examiner

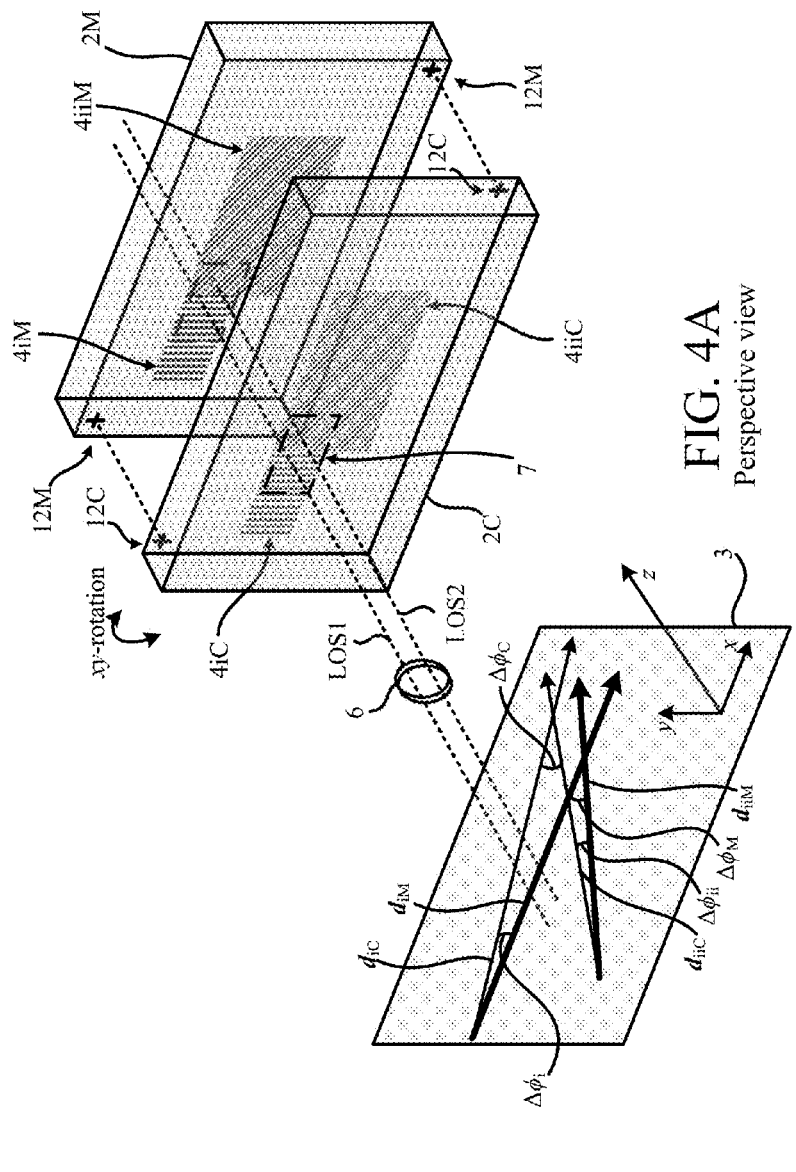
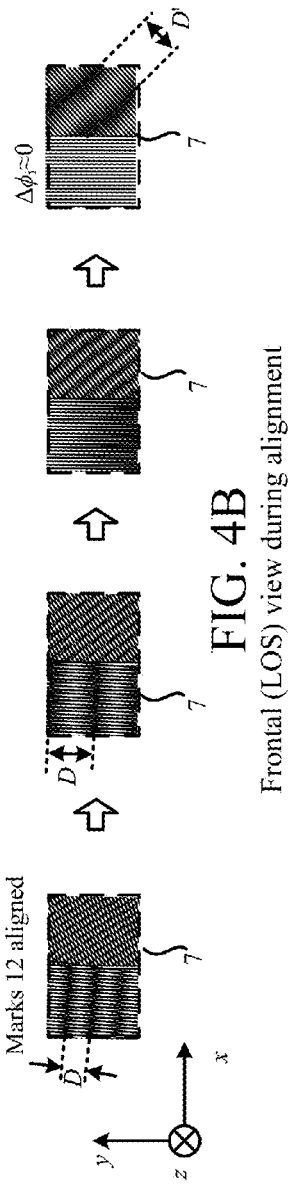
FIG. 4A
Perspective view
FIG. 4B
Frontal (LOS) view during alignment

OPTICAL COMPONENTS

BACKGROUND

Optical components can be used in optical systems to alter the state of visible light in a predictable and desired manner, for example in display systems to make a desired image visible to a user. Optical components may also be used as e.g. moulds for making other optical components. Optical components can interact with light by way of reflection, refraction, diffraction etc. Diffraction occurs when a propagating wave interacts with a structure, such as an obstacle or slit. Diffraction can be described as the interference of waves and is most pronounced when that structure is comparable in size to the wavelength of the wave. Optical diffraction of visible light is due to the wave nature of light and can be described as the interference of light waves. Visible light has wavelengths between approximately 390 and 700 nanometers (nm) and diffraction of visible light is most pronounced when propagating light encounters structures similar scale e.g. of order 100 or 1000 nm in scale. One example of a diffractive structure is a periodic diffractive structure. Periodic structures can cause diffraction of light which is typically most pronounced when the periodic structure has a spatial period of similar size to the wavelength of the light. Types of periodic structures include, for instance, surface modulations on a surface of an optical component, refractive index modulations, holograms etc. Herein, a "diffraction grating" (or simply "grating") means any (part of) an optical component which has a diffractive periodic structure. A diffraction grating has a grating period, which is the distance over which its structure repeats. When propagating light encounters the periodic structure, diffraction causes the light to be split into multiple beams in different directions. These directions depend on the wavelength of the light thus diffractions gratings cause dispersion of polychromatic (e.g. white) light, whereby the polychromatic light is split into different coloured beams travelling in different directions.

When the period structure is on a surface of an optical component, it is referred to a surface grating. When the periodic structure is due to modulation of the surface itself, it is referred to as a surface relief grating (SRG). An example of a SRG is uniform straight grooves in a surface of an optical component that are separated by uniform straight groove spacing regions. Groove spacing regions are referred to herein as "lines", "grating lines" and "filling regions". The nature of the diffraction by a SRG depends both on the wavelength of light incident on the grating and various optical characteristics of the SRG, such as line spacing, groove depth and groove slant angle. SRGs have many useful applications. One example is an SRG light guide application. A light guide (also referred to herein as a "waveguide") is an optical component used to transport light by way of internal reflection e.g. total internal reflection (TIR) within the light guide. A light guide may be used, for instance, in a light guide-based display system for transporting light of a desired image from a light engine to a human eye to make the image visible to the eye.

In the case of a waveguide-based display system, different gratings forming part of the same waveguide may serve various functions. Waveguide-based display systems typically comprise a light engine, which collimates light of an image into collimated input beams which form a virtual version of that image at infinity. The input beams may be directed towards an incoupling grating of the waveguide, which is arranged to couple them into the waveguide at angles which are sufficiently steep to cause TIR of the incoupled beams within the waveguide. An outcoupling (exit) grating on the waveguide may receive the incoupled beams internally and diffract them outwardly in directions that match the input beams (so that they form the same virtual version of the image). A user's eye can then reconstruct the image when looking at the exit grating. Usually, the exit grating is also arranged to provide beam expansion of the outputted beams so as to provide an eyebox of increased size compared with viewing the light engine directly. Intermediate grating(s) of the same waveguide may provide additional beam expansion to further increase the size of the eyebox.

For some such waveguide grating arrangements, the incoupling, outcoupling and (where applicable) intermediate grating(s) will only manipulate the image light as intended if their various gratings are oriented relative to one another in a specific manner. Deviation from this intended orientation can cause degradation of the final image as perceived by the user. When such waveguides are manufactured in bulk for incorporation in different waveguide display systems, each should preserve these specific relationships to avoid degrading the quality of the final display systems. Other types of optical component with various applications may also comprise different gratings where it is desirable for the relative orientation of those gratings to match a desired value as closely as possible.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Nor is the claimed subject matter limited to implementations that solve any or all of the disadvantages noted in the Background section.

The disclosure considers an optical component comprising an arrangement of a first and a second component grating having a component relative orientation angle. The quality of the optical component is assessed in terms of a deviation of the component relative orientation angle from a desired relative orientation angle. A quality assessment is made by comparing the optical component to a master component comprising a substantially matching arrangement of a first and a second optically transmissive master grating having the desired relative orientation angle.

When the optical and master components are supported with the first and second component gratings in the vicinity of the first and second master gratings, a first fringe pattern is formed by the first gratings as their relative orientation angle (first relative orientation angle) is changed towards zero, the fringe spacing of which increases as that first relative orientation angle decreases. Similarly, a second fringe pattern is formed by the second gratings as their relative orientation angle (second relative orientation angle) is changed towards zero, the fringe spacing of which also increases as that second relative orientation angle decreases. The disclosure recognizes that, when the fringe spacing of the first fringe pattern is substantially maximal (the first relative orientation angle thus being substantially zero), the fringe spacing of the second fringe pattern—which is indicative of the second relative orientation angle in general—is also indicative of the deviation of the component relative orientation angle from the desired relative orientation angle (as this deviation is substantially equal to the second relative orientation angle when the first relative orientation angle is substantially zero), and is thus indicative of the quality of the optical component.

A first aspect is directed to a quality assessment apparatus for assessing the quality of such an optical component. The apparatus comprises a configurable support system, a light sensor, a drive mechanism and a controller. The support system is configured to support such an optical and such a master component with the first and second component gratings of the optical component in the vicinity of the first and second master gratings of the master component. The light sensor is configured to receive light which has interacted with both of the first and light which has interacted with both of the second gratings, and to generate sensor data from the received light. The drive mechanism is coupled to the support system. The controller is configured to control the drive mechanism based on the sensor data to reconfigure the support system from a current configuration to a new configuration in which the fringe spacing of a first fringe pattern formed by the first gratings is substantially maximal. In addition, the controller is configured to measure from the sensor data the fringe spacing of a second fringe pattern formed by the second gratings in the new configuration, and to output a quality assessment based on the measured fringe spacing which is indicative of the deviation of the component relative orientation angle from the desired relative orientation angle.

Second and third aspects are directed to a quality assessment process, and a computer program product comprising code configured, when executed, to implement that process. Such an optical component and such a master component are supported by a configurable support system with the first and second component gratings of the optical component in the vicinity of the first and second master gratings of the master component. The process comprises the following. Sensor data is received, the sensor data generated from light which has interacted with both of the first gratings and light which has interacted with both of the second gratings. The support system is reconfigured based on the sensor data from a current configuration to a new configuration, in which the fringe spacing of a first fringe pattern formed by the first gratings is substantially maximal. The fringe spacing of a second fringe pattern formed by the second gratings in the new configuration is measured from the sensor data. A quality assessment is outputted based on the measured fringe spacing which is indicative of the deviation of the component relative orientation angle from the desired relative orientation angle.

BRIEF DESCRIPTION OF FIGURES

FIG. 4A is a perspective view of the optical component and the master component during a quality assessment process;

FIG. 4B shows fringe patterns observed at different points in time during the quality assessment process;

DETAILED DESCRIPTION

Figure 1A:
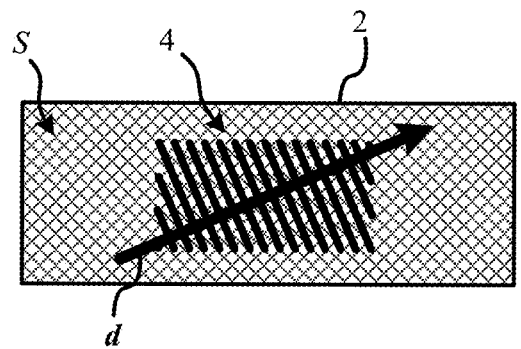
FIG. 1A is a frontal view of an optical component.
Figure 1B:
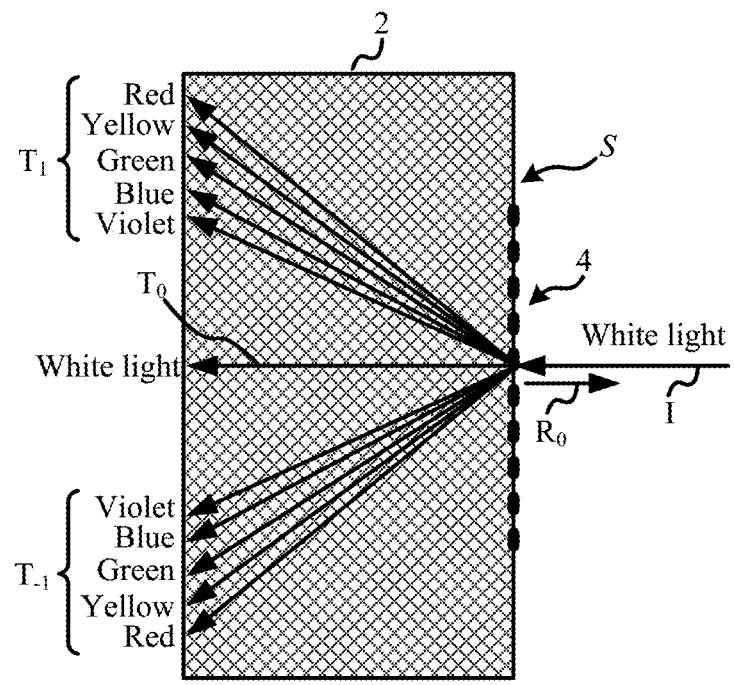
FIG. 1B is a schematic illustration of an optical component, shown interacting with incident light and viewed from the side.

FIGS. 1A and 1B show from the top and the side respectively an optical component 2, such as a waveguide or a mould for making other optical components, having an outer surface S. The optical component is optically transmissive in this embodiment, but may not be optically transmissive in other embodiments. The optical component 4 comprises a grating 4, formed by (that is, whose periodic structure arises as a result of) surface modulations over the surface S, which constitute a surface grating (specifically, an SRG). The modulations comprise grating lines which are substantially parallel and elongate (substantially longer than they are wide), and also substantially straight in this example (though they need not be straight in general).

FIG. 1B shows the optical component 2, and in particular the grating 4, interacting with an incoming illuminating light beam I that is inwardly incident on the grating 4. The light I is white light in this example, and thus has multiple colour components. The light I interacts with the grating 4 which splits the light into several beams directed inwardly into the optical component 2. Some of the light I may also be reflected back from the surface S as a reflected beam R0. A zero-order mode inward beam T0 and any reflection R0 are created in accordance with the normal principles of diffraction as well as other non-zero-order (±n-order) modes (which can be explained as wave interference). FIG. 1B shows first-order inward beams T1, T−1; it will be appreciated that higher-order beams may or may not also be created depending on the configuration of the optical component 2. Because the nature of the diffraction is dependent on wavelength, for higher-order modes, different colour components (i.e. wavelength components) of the incident light I are, when present, split into beams of different colours at different angles of propagation relative to one another as illustrated in FIG. 1B.

Figure 2A:
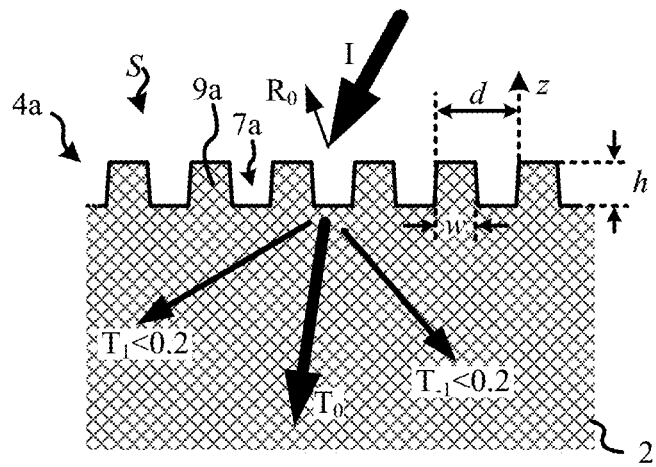
FIG. 2A is a schematic illustration of a straight binary grating, shown interacting with incident light and viewed from the side.
Figure 2B:
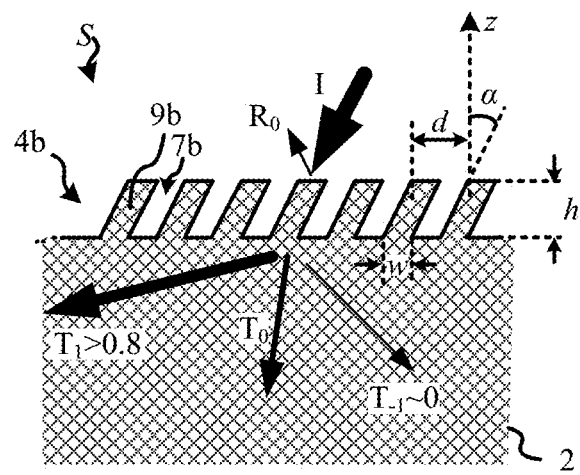
FIG. 2B is a schematic illustration of a slanted binary grating, shown interacting with incident light and viewed from the side.
Figure 2C:
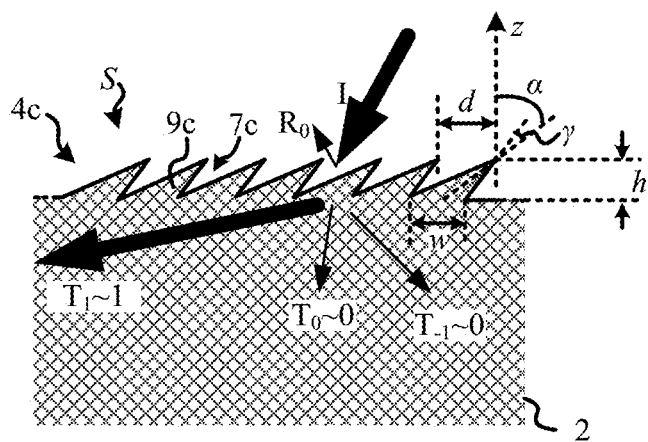
FIG. 2C is a schematic illustration of an overhanging triangular grating, shown interacting with incident light and viewed from the side.

FIGS. 2A-2C are close-up schematic cross sectional views of different exemplary gratings 4a-4c (collectively referenced as 4 herein), formed by modulations of the surface S of the optical component 2 (which is viewed from the side in these figures). Light beams are denoted as arrows whose thicknesses denote approximate relative intensity (with higher intensity beams shown as thicker arrows).

FIG. 2A shows an example of a straight binary grating 4a. The straight binary grating 4a is formed by a series of grooves 7a in the surface S separated by protruding groove spacing regions 9a which are also referred to herein as "filling regions", "grating lines" or simply "lines". The grating 4a has a spatial period of d (referred to as the "grating period"), which is the distance over which the modulations' shape repeats. The grooves 7a have a depth h and have substantially straight walls and substantially flat bases. As such, the filling regions have a height h and a width that is substantially uniform over the height h of the filling regions, labelled "w" in FIG. 2A (with w being some fraction f of the period: w=f*d).

For a straight binary grating, the walls are substantially perpendicular to the surface S. For this reason, the grating 4a causes symmetric diffraction of incident light I that is entering perpendicularly to the surface, in that each +n-order mode beam (e.g. T1) created by the grating 4a has substantially the same intensity as the corresponding −n-order mode beam (e.g. T−1), typically less than about one fifth (0.2) of the intensity of the incident beam I.

FIG. 2B shows an example of a slanted binary grating 4b. The slanted grating 4b is also formed by grooves, labelled 7b, in the surface S having substantially straight walls and substantially flat bases separated by lines 9b of width w. However, in contrast to the straight grating 4a, the walls are slanted by an amount relative to the normal, denoted by the angle α in FIG. 2B. The grooves 7b have a depth h as measured along the normal. Due to the asymmetry introduced by the non-zero slant, ±n-order mode inward beams travelling away from the slant direction have greater intensity that their $\mp$ n-order mode counterparts (e.g. in the example of FIG. 2B, the T1 beam is directed away from the direction of slant and has usually greater intensity than the T−1 beam, though this depends on e.g. the grating period d); by increasing the slant by a sufficient amount, those $\mp$n counterparts can be substantially eliminated (i.e. to have substantially zero intensity). The intensity of the T0 beam is typically also reduced very much by a slanted binary grating such that, in the example of FIG. 2B, the first-order beam T1 typically has an intensity of at most about four fifths (0.8) the intensity of the incident beam I.

The binary gratings 4a and 4b can be viewed as being formed by spatial waveforms embedded in the surface S that have a substantially square wave shape (with period d). In the case of the grating 4b, the shape is a skewed square wave shape skewed by α.

FIG. 2C shows an example of an overhanging triangular grating 4c which is a special case of an overhanging trapezoidal grating. The triangular 4c is formed by grooves 7c in the surface S that are triangular in shape (and which thus have discernible tips) and which have a depth h as measured along the normal. Filling regions 9c take the form of triangular, tooth-like protrusions (teeth), having medians that make an angle α with the normal (α being the slant angle of the grating 4c). The teeth have tips that are separated by d (which is the grating period of the grating 4c), a width that is w at the base of the teeth and which narrows to substantially zero at the tips of the teeth. For the grating of FIG. 4c, w≈d, but generally can be w<d. The grating is overhanging in that the tips of the teeth extend over the tips of the grooves. It is possible to construct overhanging triangular grating gratings that substantially eliminate both the transmission-mode T0 beam and the $\mp$ n-mode beams, leaving only ±n-order mode beams (e.g. only T1). The grooves have walls which are at an angle γ to the median (wall angle). The grating 4c can be viewed as formed by a spatial waveform embedded in S that has a substantially triangular wave shape, which is skewed by α.

The grooves and spacing regions that form the gratings 4a-4c constitute surface modulations.

Other type of grating are also possible, for example other types of trapezoidal grating patterns (which may not narrow in width all the way to zero), sinusoidal grating patterns etc. and have a modulation width that can be readily defined in a suitable manner. Such other patterns also exhibit depth h, linewidth w, slant angle α and wall angles γ which can be defined in a similar manner to FIG. 2A-C.

A grating 4 has a grating vector (generally denoted as d), whose size (magnitude) is 2π/d, and which is in a direction perpendicular to the grating lines which form that grating—see FIG. 1A.

In light guide-based display applications (e.g. where SRGs are used for coupling of light into and out of a light guide of the display system, and/or for providing beam expansion of beams coupled into the waveguide), d is typically between about 250 and 500 nm, and h between about 30 and 400 nm. The slant angle α is typically between about −45 and 45 degrees and is measured in the direction of the grating vector.

Figure 3A:
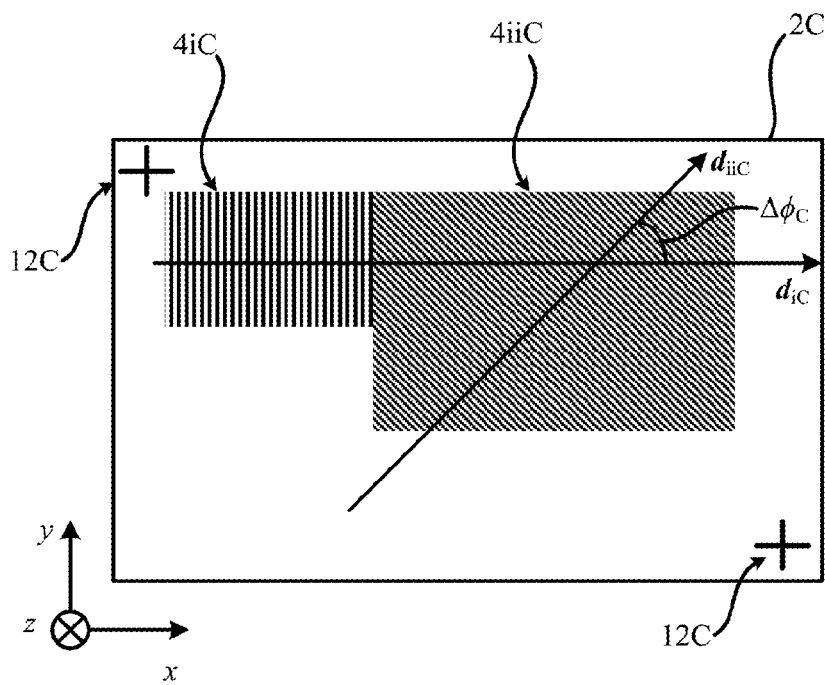
FIG. 3A is a frontal view of an optical component comprising an arrangement of gratings.

FIG. 3A shows a frontal view of an optical component 2C. The optical component 2C is of the general type described above, and comprises a fixed arrangement of a first and a second component grating 4iC, 4iiC, which can be of any of the general types discussed above. Herein, a fixed arrangement of gratings means that at least the orientation of those gratings relative to one another is fixed. The gratings 4iC, 4iiC are optically transmissive parts of the optical component 2C; that is, at least those parts are formed of optically transmissive material that allows at least some light to pass through the component gratings 4iC, 4iiC (all the way through the optical component 2C) in a direction generally normal to the gratings (parallel to the z-axis shown in FIG. 3A). In this example, the gratings 4iC, 4iiC lie substantially parallel to the same plane (xy-plane). The gratings 4iC, 4iiC are formed by surface modulations (specifically, lines and grooves) over respective portions of the optical component's surface, each lying substantially parallel to the xy-plane. The surface modulations are on frontal surface portions of the optical component 2C from the viewpoint of FIG. 3 (in alternative optical component 2C, one of the gratings may be formed by reward surface modulations on a rear surface portion instead).

The optical component 2C may be a mass-produced optical components (that is, one of a large number of optical components produced in bulk e.g. in a factory set-up), in which for example the optical component 2C is moulded from polymer.

As indicated above, in various applications, it is desirable for different gratings of the same optical component to have orientations relative to one another that match a desired orientation as closely as possible (e.g. some idealized relationship, at which the performance of the optical component is optimized with respect to its intended functions, which may be revealed though a suitable mathematical analysis).

For example, in one type of known display system—in which an incoupling, intermediate and exit grating of an optical component (which acts as a waveguide) function in tandem to cause two-dimensionally expanded versions of beams incoupled at the incoupling grating to be outputted at the exit grating—the incoupling and exit gratings should have a relative orientation angle 2ρ (i.e. relative to one another) which is double that of the incoupling and intermediate gratings (itself ρ). Moreover, that relative orientation angle ρ of the incoupling and intermediate gratings (i.e. relative to one another) should have a specific relationship with the grating periods $d_1$, $d_2$ of the incoupling and intermediate gratings, namely $\rho = \arccos(d_1/(2d_2))$. Deviation from these relationships can cause degradation in the quality of the final image as perceived by the user. Hence, the relationships should be preserved as closely as possible to ensure that the waveguide does not significantly degrade the image.

However, in practice and particularly in the context of mass-manufacturing, it can be difficult to ensure that all such optical components are manufactured to the same standard of quality. Various inaccuracies and imprecisions can develop in the manufacturing set-up which can cause degradation of the final products. Such inaccuracies and imprecisions can be difficult to detect, and become increasingly so as the scale of the manufacturing operation is increased. Of particular concern in the present context is degradation in the form of misalignment of different gratings on the same optical component.

Hereinbelow, techniques are presented which facilitate an automatic quality assessment that is both quick and reliable, in which the quality of an optical component (e.g. 2C) comprising at least two gratings (e.g. 4iC, 4iiC) is assessed in terms of a deviation of their actual relative orientation (relative to one another) from a desired relative orientation e.g.

that at which the performance of the optical component 4C is optimized with respect to its intended function.

To this end, a comparison is made between the optical component 2C and a high-quality master component 2M, which is itself a high-quality optical component but the nature of which may make it unsuitable for use in mass-manufactured end-products (e.g. because to do so would be too costly and/or time-consuming). The master component 2M is shown in FIG. 3B.

Figure 3B:
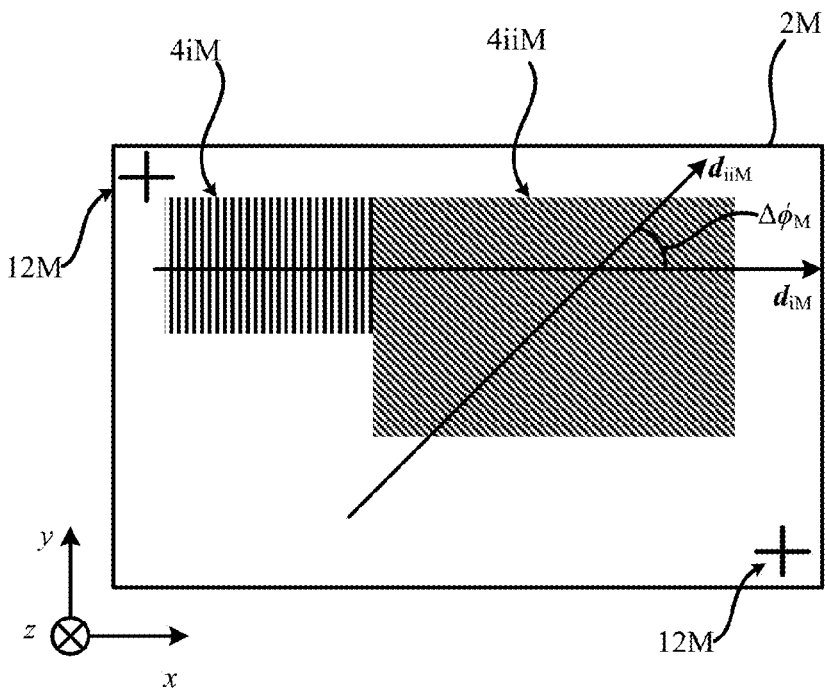
FIG. 3B is a frontal view of a master component comprising a substantially matching arrangement of gratings.

As shown in FIG. 3B, the master component 2M comprises a fixed arrangement of gratings, which are first and second master gratings 4iM, 4iiM, also of the general type discussed above and which are optically transmissive in the same manner as the component gratings 4iC, 4iiC (though in other embodiments they may not be optically transmissive). The grating arrangement of the master component 2M substantially matches the grating arrangement of the optical component 2C; that is, the master grating arrangement is such that the master gratings 4iM, 4iiM have approximately (though not necessarily exactly) the same orientation relative to one another as the component gratings 4iC, 4iiC, the first master grating 4iM (resp. second master grating 4iiM) substantially matches the first component grating 4iC (resp. second component grating 4iiC) and, moreover, when the master component 2M is placed at a location forward of the optical component 2C at which at least part of the first component grating 4iC is observable through the first master grating 4iM, at least part of the second component grating 4iiC is observable through the second master grating 4iiM at the same time. Note that "observable" in this context simply means that there exists a line of sight in the general ±z-direction that intersects both first gratings 4iC, 4iM (resp. both second gratings 4iiC, 4iiM), along which light can propagate through both components 2C, 2M so as to interact with both first gratings 4iC, 4iM (resp. both second gratings 4iiC, 4iiM), which light is detectable upon exiting the components 2C, 2M having interacted thus. In this case, the master component 2M of FIG. 3A, the master gratings 4iM, 4iiM also lie substantially parallel to the xy-plane when the optical and master components 2C, 2M are suitably aligned relative to one another.

The master component 2M may have substantially the same overall shape as the optical component 2C and/or substantially the same overall optical characteristics, though this is not required.

The master component 2M may, for instance, be formed of fused silica or some other suitable material that has been subject to a microfabrication process, in which the master gratings 4iM, 4iiM are formed by etching of and/or deposition on the surface of the material. Using such microfabrication processes, it is possible to create master gratings 4iM, 4iiM having the desired relative orientation to a very high level of accuracy (i.e. of very high quality, as the term is used herein), which can be verified by performing suitable tests on the master gratings to measure the relative orientation of the master gratings to ensure that it is indeed precisely the desired orientation and/or by testing the optical characteristics of the master gratings to ensure that the master component functions in same the manner in which the to-be-tested optical components are intended to function. Such tests, whilst generally accurate, tend to be costly and time-consuming, and thus not suitable per-se for application to mass-produced optical components. However, once it has been verified that the master component 2M is of the requisite high quality, as indicated, the quality of such mass-manufactured optical components (e.g. 2C) can be assessed quickly and reliably by way of comparison with the master component 2M in the manner set out below.

Returning to FIG. 3A, the first component grating has a grating vector $d_{iC}$ (first component grating vector) and the second component has a second grating vector $d_{iiC}$ (second component grating vector), each parallel to the respective grating lines of the relevant grating and lying in the plane of that grating. An angle $\Delta\phi_C$ is shown, which is the angle between the component grating vectors $d_{iC}$, $d_{iiC}$ as measured in the xy-plane and which is referred to herein as the relative orientation angle of the first and second component gratings 4iC, 4iiC or simply as the "component relative orientation angle"—it is this angle which is intended to precisely match a desired relative orientation angle, and the processes described herein provide an automatic assessment of the extent to which that match has been realized in practice.

Returning to FIG. 3B, the first master grating has a grating vector $d_{iM}$ (first master grating vector) and the second component has a second grating vector $d_{iiM}$ (second master grating vector), each perpendicular to the respective grating lines of the relevant grating and lying in the plane of that grating. An angle $\Delta\phi_M$ is shown, which is the angle between the master grating vectors $d_{iM}$, $d_{iiM}$ as measured in the xy-plane and which is referred to herein as the relative orientation angle of the first and second master gratings 4iM, 4iiM—it is this angle which is known to be the desired relative orientation angle to a high level of precision, and the quality of the (e.g. mass-produced) optical component 4C is assessed in terms of the size of a deviation of $\Delta\phi_C$ from $\Delta\phi_M$ i.e. in terms of $|\Delta\phi_C - \Delta\phi_M|$. When this deviation is substantially zero, the quality of the optical component 2C is considered to be optimal.

The optical and master components each comprise respective alignment marks 12C, 12M shown in FIGS. 3A and 3B respectively. The alignments marks are arranged such that, when the master component 2M is moved forward of the optical component 2C to bring the master marks of 12C into alignment with the component marks 12M when viewed in the z-direction, the first master grating 4iM is at least approximately aligned (by angle) with the first component grating 4iC. This is discussed below.

A quality assessment process will now be described with reference to FIGS. 4A and 4B.

FIG. 4A is a perspective view of the master and optical components 2M, 2C during the process, in which the xy-plane 3 is shown. The master component 12M is supported forward of the optical component 12C and substantially parallel to the xy-plane, with the first component grating 4iC opposing the first master grating 4iM, and the second component grating 4iiC opposing the second master grating 4iiM. In this configuration, the first gratings 4iC, 4iM lie substantially parallel to the same plane as one another (which is the xy-plane 3), and the second gratings 4iiC, 4iiM also lie substantially parallel to the same plane as one another (which is also the xy-plane 3).

The respective geometric projections of the component grating vectors $d_{iC}$, $d_{iiC}$ and master grating vectors $d_{iM}$, $d_{iiM}$ in the xy-plane 3 are shown. Note that herein (including in the figures), the notation $d_{iC}$, $d_{iiC}$, $d_{iM}$, $d_{iiM}$ is used interchangeably to denote both the grating vectors themselves and the geometric projections of the grating vectors in the xy-plane, and it will be clear from the context which is meant. For the sake of clarity, the master projections $d_{iM}$, $d_{iiM}$ are represented by thicker arrows than the component projections $d_{iC}$, $d_{iiC}$ in FIG. 4A.

In addition to the relative orientation angle $\Delta\phi_C$ of the first and second component gratings 4iC, 4iiC (which is an inherent property of the optical component 2C) and the relative orientation angle $\Delta\phi_M$ of the first and second master gratings 4iM, 4iM (which is an inherent property of the master component 2M), an angle $\Delta\phi_i$ is shown, which is the angle between the first master grating vector $d_{iM}$ and the first component grating vector $d_{iC}$ as measured in the xy-plane 3, and which is referred to herein as the relative orientation angle of the first gratings 4iM, 4iC or simply as the "first relative orientation angle". Another angle $\Delta\phi_{ii}$ is shown, which is the angle between the second master grating vector $d_{iiM}$ and the second component grating vector $d_{iiC}$ as measured in the xy-plane, and which is referred to herein as the relative orientation angle between the second gratings 4iiM, 4iiC or simply as the "second relative orientation angle". The angles $\Delta\phi_i$, $\Delta\phi_{ii}$ are properties of the current orientation of the optical component 2C relative to the master component 2M, and change as that orientation is changed.

A first line of sight (LOS1) is shown, which lies substantially parallel to the z-axis and which intersects both the first gratings 4iC, 4iM of the optical and master components 2C, 2M respectively. A second line of sight (LOS2) is shown, which also lies substantially parallel to the z-axis but which intersects both the second gratings 4iiC, 4iiM of the optical and master components 2C, 2M respectively.

The disclosure recognizes that, when the optical component 2C and the master component 2M are held in a relative xy-orientation such that the first relative orientation angle $\Delta\phi_i$ of the first gratings 4iC, 4iM is substantially zero (substantially perfect alignment)—which can be achieved by effecting xy-rotation of one or both of the master and optical component 2M, 2C—the size of the second relative orientation angle $|\Delta\phi_{ii}|$ of the second gratings 4iiC, 4iiM will be substantially equal to $|\Delta\phi_C - \Delta\phi_M|$ i.e. the size of the deviation of the component relative orientation angle $\Delta\phi_C$ of the component gratings 4iC, 4iiC from the desired relative orientation angle $\Delta\phi_M$ that separates the master gratings 4iM, 4iiM, which as discussed above is precisely the quantity that is indicative of the quality of the optical component 2C. The size of the second relative orientation angle at a point in time when $\Delta\phi_i = 0$ is denoted $|\Delta\phi_{ii}|_{\Delta\phi_i = 0} = |\Delta\phi_C - \Delta\phi_M|$. When $|\Delta\phi_{ii}|_{\Delta\phi_i = 0} = |\Delta\phi_C - \Delta\phi_M| = 0$, the optical component 2C is considered to have optimal quality, with larger $|\Delta\phi_{ii}|_{\Delta\phi_i = 0} = |\Delta\phi_C - \Delta\phi_M|$ being considered lower quality.

In changing the relative xy-orientation of the two components 2C, 2M, the orientation $\Delta\phi_C$ of the component gratings 4iC, 4iiC relative to one another is unchanged, as is the orientation $\Delta\phi_M$ of the master gratings 4iM, 4iiM relative to one another (these being inherent properties of the respective components). In contrast, what is changed is the orientation of the component gratings relative to the master gratings—in particular the orientation $\Delta\phi_i$ of the first component grating 4iC relative to the first master grating 4iM, and the orientation of the $\Delta\phi_{ii}$ of the second component grating 4iC relative to the second master grating 4iM, which are each changed by substantially the same amount when the xy-orientation of the components 2C, 2M is changed from a current xy-orientation to a new xy-orientation.

The disclosure further recognizes that, when the first gratings are in near, but not perfect alignment—e.g. about (5/100)° ≤ $\Delta\phi_i$ ≤ about (1/1000)° (near alignment range)—a first fringe pattern will be visible along the first line of sight LOS1, that pattern formed by light which has propagated through or been reflected from, and which has thus interacted with, both first gratings 4iC, 4iM, which are effectively overlaid on one another when viewed along the first line of sight LOS1. The first fringe pattern exhibits a fringe spacing that increases as $\Delta\phi_i$ decreases, becoming maximal (theoretically infinite) when $\Delta\phi_i = 0$. When $\Delta\phi_i$ is within approximately the aforementioned approximate near alignment range, the fringe spacing will be measurable i.e. such that the fringes are neither too small nor too large to be undetectable. For example, when $\Delta\phi_i \approx (5/1000)°$, the fringe pattern will typically have a fringe spacing around 2 mm, which is readily observable. The period of the fringe pattern is $\approx d/\Delta\phi$ (the approximation is very accurate with small angles), with d the grating period and $\Delta\phi$ in radians. The fringes appear perpendicular to the grating lines.

Eventually, as $\Delta\phi_i$ tends towards zero, it will become sufficiently small that the fringes become larger than the surface area of the first gratings (or at least larger than a portion that area if only that portion is being observed). Typically, this will occur around $\Delta\phi_i \approx (1/1000)°$, at which point the fringe spacing is considered substantially maximal and $\Delta\phi_i$ substantially zero—by adjusting the relative xy-orientation alignment of the optical and master component 2C, 2M from an initial configuration to the point at which that substantially maximal fringe spacing is reached (new configuration), it is thus possible to align the first gratings 4iC, 4iM to that level of accuracy. Moreover, when the first gratings 4iC, 4iM are thus aligned in the new configuration with $\Delta\phi_i$ substantially zero, provided $|\Delta\phi_{ii}|_{\Delta\phi_i = 0}$ is itself with the aforementioned approximate near alignment range, a second fringe pattern will also be visible along the second line of sight LOS2, formed in an equivalent manner by light which has passed through or reflected from the surfaces with gratings and thus interacted with both of the second gratings 4iiC, 4iiM, which are similarly effectively overlaid on one another when viewed along the second line of sight LOS2. The larger the fringe spacing of the second fringe pattern in the new configuration, the smaller $|\Delta\phi_{ii}|_{\Delta\phi_i = 0} = |\Delta\phi_C - \Delta\phi_M|$. That is, the larger the fringe spacing of the second fringe pattern in the new configuration, the higher the quality of the optical component 2C i.e. the smaller the deviation of the component relative orientation angle $\phi_C$ between the two component gratings 4iC, 4iiC from the desired relative orientation angle $\phi_M$ between the corresponding master gratings 4iM, 4iiM.

This is illustrated in FIG. 4B, which shows exemplary first and second fringe patterns as visible over an area 7 (also shown in FIG. 4A), as viewed generally along the lines of sight LOS1, LOS2. The fringe patterns are shown in FIG. 7B at various points in time during the quality assessment process.

The far-left hand side of FIG. 4B shows a view of the area 7 when the components 2C, 2M are in an initial configuration, in which the first gratings 4iC, 4iM of the optical and master component 2C, 2M are in near alignment. In this example, the initial configuration is achieved by aligning the alignment marks 12C of the optical component 2C with the corresponding alignment marks 12M of the master component 2M as viewed in a direction generally parallel to the z-axis (intermediate configuration), which alignment marks 12C, 12M are such that, when so aligned in the intermediate configuration, $\Delta\phi_i$ is within the aforementioned approximate near alignment range. The optical component 2C can be provided with the alignments 12M marks at the time of its manufacturing process (e.g. for a moulded optical component, alignment mark structure can be included on the same mould from which the grating structure is imparted). Typically, the nature of the manufacturing process in question means that, notwithstanding potential imprecisions/inaccuracies of the kind being tested for by the present process, it is possible to provide suitable alignment marks that can be used to achieve such near alignment within the near alignment range.

Alternatively, the process may be performed without alignment marks, and the xy-orientation of the two components 2C, 2M can simply be scanned from any arbitrary starting point until the first fringe pattern becomes visible (such scanning could also be used if, for some reason, $\Delta\phi_i$ is not in fact within the approximate near alignment range even when such alignment marks are so aligned e.g. due to unexpectedly large manufacturing errors). Typically, the use of alignment marks reduces the time it takes to make the quality assessment, which can be particularly significant in terms of the overall efficiency of the process when there are a large number of optical components to be assessed.

Once near alignment of the first gratings 4iC, 4iM has been so achieved, the xy-orientation of the component 2C, 2M is fine tuned to a new configuration in which the fringe spacing of the first fringe pattern (indicated by a distance labelled D in FIG. 4B) is substantially maximal and thus in which $\Delta\phi_i \approx 0$—this is shown on the far right of FIG. 4B. The intervening views of FIG. 4B represent the changing view as the components 2M, 2C are moved to change their xy-orientation from the initial configuration on the far-left to the new configuration on the far-right. The fringe spacing of the second fringe pattern (indicated by a distance labelled D' in FIG. 4B) in the new configuration can then be measured, and the measured fringe spacing used to output a quality assessment, with the quality assessment indicating lower (resp. higher) quality the smaller (resp. larger) the measured fringe spacing.

Should the fringe spacing of the second fringe pattern in the new configuration be substantially zero (i.e. should both the fringe spacing of the first fringe pattern and the fringe spacing of the second fringe pattern be substantially zero simultaneously), that indicates there to be substantially no deviation of $\phi_C$ from $\phi_M$ and that the optical component 2C is thus of substantially optimal quality.

Although FIG. 4A shows the fringe patterns as having been created by light which has passed though both gratings by way of example, it is not required that light passes through both plates (thus the optical components do not have to be optically transmissive) for the fringe patterns to appear so the gratings—the patterns can be formed of reflected light (e.g. light of reflective diffraction modes). In practice the fringe patterns are usually most visible when the light is reflected from the surfaces of the gratings as compared with a situation in which the light passes through both.

Figure 5:
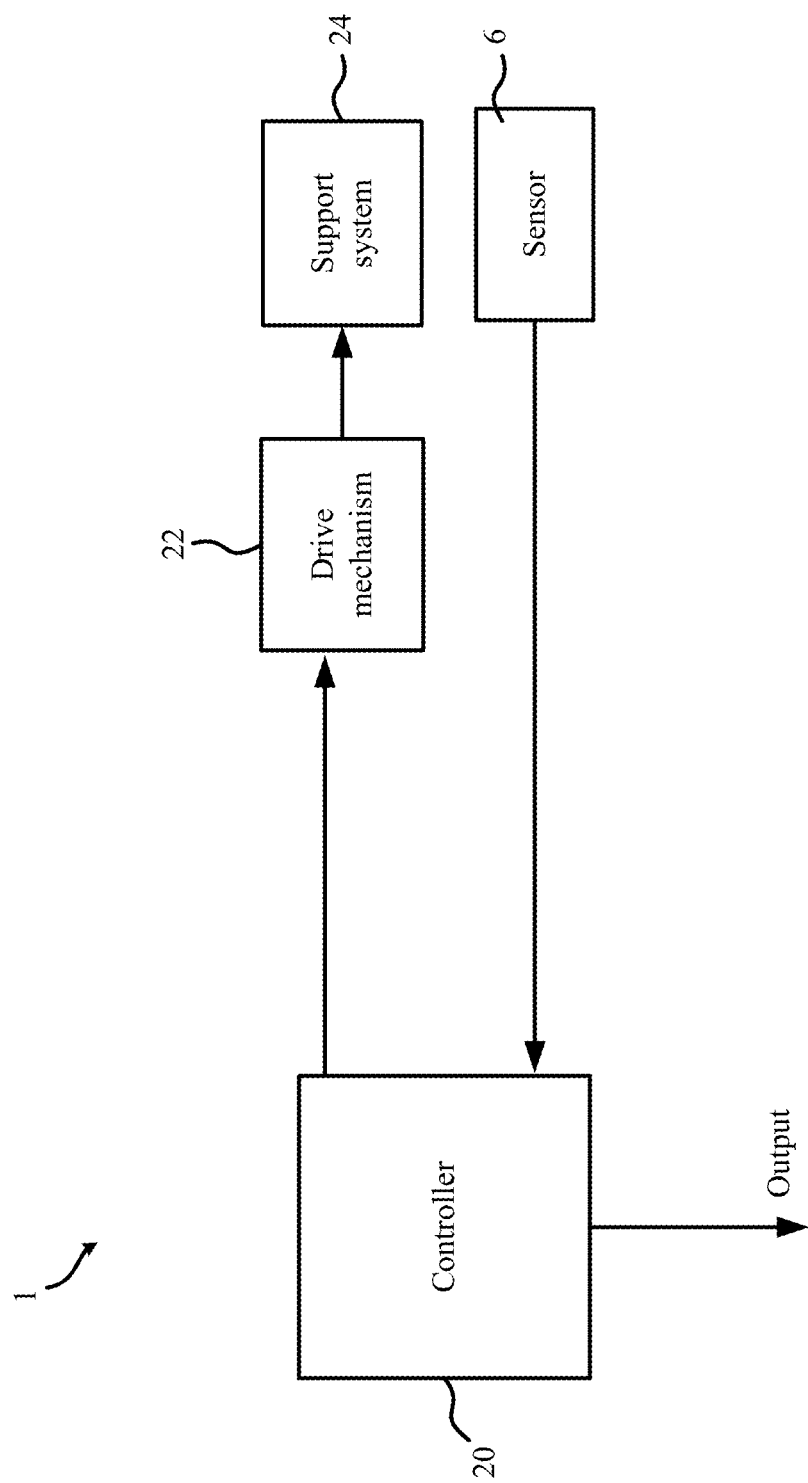
FIG. 5 is a block diagram of a quality assessment apparatus.

FIG. 5 is a block diagram of the quality assessment apparatus 1, which comprises a controller 20, a drive mechanism 22, a configurable support system 24 and a sensor 6 (which is also shown in FIG. 4A, disposed along the lines of sight LOS1, LOS2).

The configurable support system 24 supports the optical and master components 2C, 2M in a configurable configuration. The system 24 can be configured to effect relative motion between the two components 2C, 2M to align the alignment marks 12C, 12M, and moreover to effect the subsequent fine-tuning—that is, to change at least the xy-orientation of the master and component to vary $\Delta\phi_i$ and $\Delta\phi_{ii}$ in the manner described above. The drive mechanism 22 is coupled to the support system 24, and is controllable to change the configuration of the system 24 in a controlled manner.

The light sensor 22 receives light from (senses) the first gratings 2iM, 2iC and from the second gratings 2iiM, 2iiC, and in particular from the second fringe patterns described above, from which it generates sensor data that is received by the controller 20.

Based on the received sensor data, the controller 20 controls the drive mechanism 22 to reconfigure the configuration of the components 2C, 2M until the sensor data indicates that the substantially maximal fringe spacing D of the first fringe pattern has been achieved. The controller 20 also measures from the sensor data the fringe spacing D' at that point in time.

Based on this measured fringe spacing, the controller 20 outputs a suitable quality assessment e.g. to an operator of the apparatus 1 via a user interface of the controller 20, or to some other component of the apparatus 1 (not shown) e.g. computer storage, in which the assessment is stored for later use.

The sensor 6 may also capture light of (that is, sense) the alignment marks 12C, 12M, and the controller 20 may—prior to performing the fine tuning reconfiguration—perform an initial reconfiguration to achieve alignment of the alignment marks 12C, 12M based on sensor data pertaining to the alignment marks as received from the sensor 6. For example, the sensor 6 may capture images of the marks 12C, 12M, on which image recognition is performed to detect those marks and to identify when the detected marks are aligned.

The controller 20 can be implemented as code executed on a suitable processor.

In practice, visibility of the fringe pattern can be increased by suitable illumination of the apparatus. For instance, to enhance the visibility of the fringe pattern, a laser (not shown) may be used to provide a beam that is directed towards the gratings 4iC, 4iM, 4iiC, 4iiM so that part passes though both the first gratings 4iC, 4iM and another part through both the second gratings 4iiC, 4iiM. A beam expander (not shown) may be used to expand the beam before reaching the gratings 4iC, 4iM, 4iiC, 4iiM, so as to increase the size of the area (e.g. 7) over which the visibility is enhanced. For example, the beam may be expanded to encompass the gratings 4iC, 4iM, 4iiC, 4iiM to provide the enhanced visibility of the fringe patterns over the full extent of the gratings 4iC, 4iM, 4iiC, 4iiM.

In a first embodiment, the sensor 6 comprises an image sensing component in the form of a camera, which supplies images of at least the area 7 to the controller 20 (such images capturing views of the type shown in FIG. 4B). The controller comprises an image recognition module which performs an automatic image recognition procedure on the received images to detect the fringes of the fringe patterns when captured in the images. The controller adjusts $\Delta\phi_i$ until the results of the image recognition procedure indicate that the fringe spacing D of the first fringe pattern is substantially maximal, and then measures the fringe spacing D' of the second fringe pattern at that point in time, again based on the results of the image recognition procedure.

The fringe spacing can be so measured in various different ways, for instance in terms of a spatial period-type metric (which is D' in FIG. 4B) or a spatial frequency-type metric e.g. by counting the number of fringes visible within a predetermined distance (lower frequency indicating larger fringes thus higher quality).

In a second embodiment, the sensor 6 comprises a first and a second photodiode (or other suitable first and second sensor components), which are shielded from surrounding light but for a respective small pinhole—e.g. having a diameter ~1 mm (order of magnitude)—through which only a small portion of the first and second fringe pattern is observable respectively. That is, such that the only light received by the first (resp. second) photodiode is from a small portion of the first (resp. second) fringe pattern the size of the respective pinhole, so that once the relevant gratings are in near alignment, the fringes are larger than the pinhole. The controller 20 then changes the xy-orientation of the component 2C, 2M, e.g. at a uniform rate. As the gratings (4iC, 4iM/4iiC, 4iiM) are brought into alignment, the fringe spacing of the relevant fringe pattern increases, which effectively results in movement of those fringes (this is evident in FIG. 4D). Thus the intensity of the light received by the photodiodes oscillates between high (when only part of a light fringe is observable through the pinhole) and low (when only part of a dark fringe is perceivable through the pinhole) as the xy-orientation of the components 2C, 2M is changed. As the fringe spacing increases, the rate of this oscillation will decrease due to the light and dark fringes becoming progressively larger so that the rate of oscillation observed by the first photodiode through the first pinhole is minimal as $\Delta\phi_i$ becomes substantially zero—in the second embodiment, the controller adjusts the xy-orientation until that minimum rate of oscillation is achieved, and measures the fringe spacing D' of the second fringe pattern in terms of the rate of oscillation observed by the second photodiode through the second pinhole at a point in time at which that minimum rate of oscillation as observed by the first photodiode through the first pinhole is achieved.

The rate of oscillation can be so measured in various different ways, for instance in terms of a temporal period-type metric e.g. obtained by timing individual oscillations or temporal frequency-type metric e.g. obtained by counting the number of oscillations that occur over an interval of predetermined length.

As mentioned, the optical component can be a mould for making other optical components. Moulds are needed in large quantities because the end product is needed in very high quantities. Thus it's also useful to have a quick method for analysing moulds.

The quality assessment outputted by the controller can take a number of forms. For example, the controller may simply output a value of the second pattern fringe spacing D' as measured at a point in time when the fringe spacing D of the first pattern is substantially zero (e.g. expressed as a measured spatial period, spatial frequency, temporal period, temporal frequency etc.) as this is directly indicative of the quality of the component. Alternatively, the controller could compute some suitable quality metric based on the measured fringe spacing, for example in the simplest case a binary metric that can take one of two values, one of which indicates acceptable quality (when the measured fringe spacing is above a predetermined threshold) and the other unacceptable quality (when the measured fringe spacing is below that threshold), though more complex quality metrics can alternatively be used to provide richer information.

Whilst in the above, the exemplary first gratings 4$i$C, 4$i$M (resp. second gratings 4$ii$C, 4$ii$M) match due to the fact that they are both formed of substantially straight grating lines, in general gratings which are considered to "substantially match" do not necessarily have to be formed of straight grating lines, nor do they have to be formed of identically shaped curved grating lines. In general, two gratings "substantially match" provided some parts of their respective structures are similar enough for it to be possible to create an observable fringe pattern that exhibits a discernible fringe spacing by overlaying those parts (even though other parts of their structure may be markedly different). Matching gratings may or may not have the same grating period.

Whilst in the above, the component gratings 4$i$C, 4$ii$C (and, correspondingly, the master gratings 4$i$M, 4$ii$M, which are in a substantially matching arrangement) are formed by modulations over substantially parallel surface portions, this does not have to be the case in general (for non-parallel gratings, the various angles shown e.g. in FIG. 4A can be equivalently defined by way of geometric projection onto a suitable plane e.g. whose normal is in the direction of the vector sum of the normals of the non-parallel gratings, which is the direction of the mean of those directions). Further, whilst in the above the surface modulations are over substantially flat surface portions, the disclosed techniques can also be applied to curved gratings e.g. formed by modulations on curved surface portions.

Further, in general the terminology "opposing gratings" (or similar) encompasses gratings which are not parallel. Two gratings are considered to be opposing when there exists a line of sight intersecting both gratings (e.g. in a direction that substantially matches the normals to those gratings), along which a resulting fringe pattern can be observed when those gratings are in near alignment. Whilst the above has been described with reference to opposing gratings, the techniques can be applied to non-opposing gratings, whereby the fringe pattern is formed for instance by a beam which has been guided onto both gratings by reflection.

The various gratings 4$i$C, 4$ii$C, 4$i$M, 4$ii$M can be binary (slanted/non-slanted), sinusoidal, trapezoidal (e.g. triangular) in shape (among others) and need not have the same shape, slant a, width w, depth h etc. as one another (though this is not excluded).

Whilst the above considers a substantially software-implemented controller 20, the functionality of the controller can be implemented using software, firmware, hardware (e.g., fixed logic circuitry), or a combination of these implementations. The terms "module," "functionality," "component" and "logic" as used herein generally represent, where applicable, software, firmware, hardware, or a combination thereof. In the case of a software implementation, the module, functionality, or logic represents program code that performs specified tasks when executed on a processor (e.g. CPU or CPUs). The program code can be stored in one or more computer readable memory devices. The features of the techniques described below are platform-independent, meaning that the techniques may be implemented on a variety of commercial computing platforms having a variety of processors.

For example, the apparatus may also include an entity (e.g. software) that causes hardware of a computer of the apparatus to perform operations, e.g., processors functional blocks, and so on. For example, the computer may include a computer-readable medium that may be configured to maintain instructions that cause the computer, and more particularly the operating system and associated hardware of the computer to perform operations. Thus, the instructions function to configure the operating system and associated hardware to perform the operations and in this way result in transformation of the operating system and associated hardware to perform functions. The instructions may be provided by the computer-readable medium to the computer through a variety of different configurations.

One such configuration of a computer-readable medium is signal bearing medium and thus is configured to transmit the instructions (e.g. as a carrier wave) to the computing device, such as via a network. The computer-readable medium may also be configured as a computer-readable storage medium and thus is not a signal bearing medium. Examples of a computer-readable storage medium include a random-access memory (RAM), read-only memory (ROM), an optical disc, flash memory, hard disk memory, and other memory devices that may us magnetic, optical, and other techniques to store instructions and other data.

In embodiments of the various aspect set out in the Summary section, the optical component and the master component may comprise alignment marks located so that, when the marks are aligned, the first fringe pattern is observable, wherein the sensor senses the marks, and wherein the controller is configured based on sensor data pertaining to the marks to reconfigure the support system from the current configuration to an intermediate configuration, in which the alignments marks are substantially aligned and from which the support system is then reconfigured to the new configuration.

The light sensor may comprise a camera which captures images of the first fringe pattern as the support system is reconfigured, and wherein the controller comprises an image recognition module which performs an automatic image recognition procedure to detect the first fringe pattern in the images, wherein the controller reconfigures the support system based on the results of the image recognition procedure.

The images may also be of the second fringe pattern, the automatic image recognition procedure detects the second fringe pattern, and the controller measures the fringe spacing of the second fringe pattern based on the results of the image recognition procedure.

The light sensor may comprise a sensor component which receives light of only a small portion of the first fringe pattern as the support system is reconfigured, and the controller may reconfigure the support system based on the rate at which the intensity of that light changes.

The light sensor may comprise another sensor component which receives light of only a small portion of the second fringe pattern, and the controller may measure the fringe spacing of the second fringe pattern based on the rate at which the intensity of that light changes.

The apparatus may comprise a laser which provides a beam and a beam expander which expands the beam to illuminate the gratings with an expanded beam that substantially encompasses the gratings so as to enhance the visibility of the fringe patterns.

The optical component and the master component may comprise alignment marks located so that, when the marks are aligned, the first fringe pattern is observable, and the process may comprise reconfiguring the support system from the current configuration to an intermediate configuration, in which the alignments marks are substantially aligned and from which the support system is then reconfigured to the new configuration.

The component gratings may be formed by surface modulations on the surface of the optical component. The surface modulations may be on substantially parallel portions of the surface of the optical component.

Both the component gratings may be formed by surface modulations on frontal portions of the surface of the optical component.

One of the component gratings may be formed by surface modulations on a frontal portion of the surface of the optical component and the other is formed by surface modulations on a rearward portion of the surface of the optical component.

The optical component may comprise polymer or may be a mould for moulding such optical components.

A microfabrication process may be performed on the master component to fabricate the master gratings prior to performing the steps of the second aspect.

The master component gratings may be tested to assess the quality of the master component prior to performing the steps of the second aspect.

The first component grating may have a period $d_1$ and the second component grating may have a period $d_2$, and the desired orientation angle of the master gratings may be substantially $\arccos(d_1/(2d_2))$.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

The invention claimed is:

1. A quality assessment apparatus for assessing the quality of an optical component, the optical component comprising an arrangement of a first and a second component grating having a component relative orientation angle, wherein the quality is assessed in terms of a deviation of the component relative orientation angle from a desired relative orientation angle, the apparatus comprising:
   a configurable support system configured to support a master component comprising a substantially matching arrangement of a first and a second master grating having the desired relative orientation angle and to support the optical component with the first and second component gratings in the vicinity of the first and second master gratings, the apparatus further comprising:
   a light sensor configured to receive light which has interacted with both of the first gratings and light which has interacted with both of the second gratings, and to generate sensor data from the received light;
   a drive mechanism coupled to the support system; and
   a controller configured (i) to control the drive mechanism based on the sensor data to reconfigure the support system from a current configuration to a new configuration in which the fringe spacing of a first fringe pattern formed by the first gratings is substantially maximal and (ii) to measure from the sensor data the fringe spacing of a second fringe pattern formed by the second gratings in the new configuration, and to output a quality assessment based on the measured fringe spacing which is indicative of the deviation of the component relative orientation angle from the desired relative orientation angle.

2. A quality assessment apparatus according to claim 1, wherein the optical component and the master component comprise alignment marks located so that, when the marks are aligned, the first fringe pattern is observable, wherein the sensor senses the marks, and wherein the controller is configured based on sensor data pertaining to the marks to reconfigure the support system from the current configuration to an intermediate configuration, in which the alignments marks are substantially aligned and from which the support system is then reconfigured to the new configuration.

3. A quality assessment apparatus according to claim 1, wherein the light sensor comprises a camera which captures images of the first fringe pattern as the support system is reconfigured, and wherein the controller comprises an image recognition module which performs an automatic image recognition procedure to detect the first fringe pattern in the images, wherein the controller reconfigures the support system based on the results of the image recognition procedure.

4. A quality assessment apparatus according to claim 3, wherein the images are also of the second fringe pattern, the automatic image recognition procedure detects the second fringe pattern, and the controller measures the fringe spacing of the second fringe pattern based on the results of the image recognition procedure.

5. A quality assessment apparatus according to claim 1, wherein the light sensor comprises a sensor component which receives light of only a small portion of the first fringe pattern as the support system is reconfigured, and the controller reconfigures the support system based on the rate at which the intensity of that light changes.

6. A quality assessment apparatus according to claim 5, wherein the light sensor comprises another sensor component which receives light of only a small portion of the second fringe pattern, and the controller measures the fringe spacing of the second fringe pattern based on the rate at which the intensity of that light changes.

7. A quality assessment apparatus according to claim 1 comprising a laser which provides a beam and a beam expander which expands the beam to illuminate the gratings with an expanded beam that substantially encompasses the gratings so as to enhance the visibility of the fringe patterns.

8. A quality assessment process for assessing the quality of an optical component, the optical component comprising an arrangement of a first and a second component grating having a component relative orientation angle, wherein the quality is assessed in terms of a deviation of the component relative orientation angle from a desired relative orientation angle, wherein the optical component and a master component comprising a substantially matching arrangement of a first and a second master grating having the desired relative orientation angle are supported by a configurable support system with the first and second component gratings in the vicinity of the first and second master gratings, the process comprising:
receiving sensor data, the sensor data generated from light received which has interacted with both of the first gratings and light which has interacted with both of the second gratings;
reconfiguring the support system based on the sensor data from a current configuration to a new configuration, in which the fringe spacing of a first fringe pattern formed by the first gratings is substantially maximal;
measuring from the sensor data the fringe spacing of a second fringe pattern formed by the second gratings in the new configuration; and
outputting a quality assessment based on the measured fringe spacing which is indicative of the deviation of the component relative orientation angle from the desired relative orientation angle.

9. A quality assessment process according to claim 8, wherein the optical component and the master component comprise alignment marks located so that, when the marks are aligned, the first fringe pattern is observable, and wherein the process comprises reconfiguring the support system from the current configuration to an intermediate configuration, in which the alignments marks are substantially aligned and from which the support system is then reconfigured to the new configuration.

10. A quality assessment process according to claim 8, wherein the component gratings are formed by surface modulations on the surface of the optical component.

11. A quality assessment process according to claim 8, wherein the surface modulations are on substantially parallel portions of the surface of the optical component.

12. A quality assessment process according to claim 8, wherein both the component gratings are formed by surface modulations on frontal portions of the surface of the optical component.

13. A quality assessment process according to claim 8 wherein one of the component gratings is formed by surface modulations on a frontal portion of the surface of the optical component and the other is formed by surface modulations on a rearward portion of the surface of the optical component.

14. A quality assessment process according to claim 8, wherein the optical component comprises polymer or is a mould for moulding such optical components.

15. A quality assessment process according to claim 8, comprising performing a microfabrication process on the master component to fabricate the master gratings prior to performing the steps of claim 8.

16. A quality assessment process according to claim 8 comprising testing the master component gratings to assess the quality of the master component prior to performing the steps of claim 8.

17. A quality assessment process according to claim 8, wherein the first component grating has a period $d_1$ and the second component grating has a period $d_2$, and the desired orientation angle of the master gratings is substantially arccos $(d_1/(2d_2))$.

18. An apparatus comprising:
one or more processors; and
a computer-readable storage medium having stored thereon code for assessing the quality of an optical component, the optical component comprising an arrangement of a first and a second component grating having a component relative orientation angle, wherein the quality is assessed in terms of a deviation of the component relative orientation angle from a desired relative orientation angle, wherein the optical component and a master component comprising a substantially matching arrangement of a first and a second master grating having the desired relative orientation angle are supported by a configurable support system with the first and second component gratings in the vicinity of the first and second master gratings, the code configured when executed by the one or more processors to cause operations comprising:
receiving sensor data, the sensor data generated from light which has interacted with both of the first gratings and light which has interacted with both of the second gratings;
reconfiguring the support system based on the sensor data from a current configuration to a new configuration, in which the fringe spacing of a first fringe pattern formed by the first gratings is substantially maximal;
measuring from the sensor data the fringe spacing of a second fringe pattern formed by the second gratings in the new configuration; and
outputting a quality assessment based on the measured fringe spacing which is indicative of the deviation of the component relative orientation angle from the desired relative orientation angle.

19. An apparatus according to claim 18, wherein the optical component and the master component comprise alignment marks located so that, when the marks are aligned, the first fringe pattern is observable, wherein the sensor data includes sensor data pertaining to the marks, and wherein the operations comprise reconfiguring, based on the sensor data pertaining to the marks, the support system from the current configuration to an intermediate configuration, in which the alignments marks are substantially aligned and from which the support system is reconfigured to the new configuration.

20. An apparatus according to claim 18 wherein the sensor data comprises images of the first fringe pattern and the operations comprise performing automatic image recognition on the images to detect the first fringe pattern, wherein a drive mechanism coupled to the support system is controlled based on the results of the image recognition procedure.

* * * * *